US012697137B2

(12) United States Patent
Ryu et al.

(10) Patent No.: US 12,697,137 B2
(45) Date of Patent: Aug. 4, 2026

(54) APPARATUS FOR INJECTING TUBE-TYPE IMPLANT INTO EYE

(71) Applicant: MICROT INC., Seoul (KR)

(72) Inventors: Junoh Ryu, Gwacheon-si (KR);
Doohwan Kwak, Yongin-si (KR);
Jiyeon Kim, Seoul (KR)

(73) Assignee: MICROT INC., Seoul (KR)

( * ) Notice: Subject to any disclaimer, the term of this patent is extended or adjusted under 35 U.S.C. 154(b) by 36 days.

(21) Appl. No.: 19/054,733

(22) Filed: Feb. 14, 2025

(65) Prior Publication Data

US 2025/0186083 A1     Jun. 12, 2025

Related U.S. Application Data

(63) Continuation of application No. PCT/KR2023/007931, filed on Jun. 9, 2023.

(30) Foreign Application Priority Data

Aug. 17, 2022     (KR) ........................ 10-2022-0102661

(51) Int. Cl.
*A61F 9/007*          (2006.01)
*A61B 17/34*          (2006.01)
(Continued)

(52) U.S. Cl.
CPC .......... *A61B 17/3468* (2013.01); *A61B 90/03* (2016.02); *A61F 2/148* (2013.01); *A61B 2090/033* (2016.02)

(58) Field of Classification Search
CPC .... A61F 9/00781; A61F 9/0017; A61F 9/007; A61M 27/002; A61B 17/3468
(Continued)

(56) References Cited

U.S. PATENT DOCUMENTS 6,558,342 B1 *  5/2003  Yaron ................. A61F 9/00781
                                                          604/9
9,289,324 B2 *  3/2016  Johnson .............. A61F 9/00781
                            (Continued)

FOREIGN PATENT DOCUMENTS

CN          114848290 A      8/2022
JP       2009-542370 A      12/2009
                    (Continued)

OTHER PUBLICATIONS

International Search Report for PCT/KR2023/007931, written Sep. 21, 2023.

*Primary Examiner* — Tuan V Nguyen
(74) *Attorney, Agent, or Firm* — ZION IP; Byungwoong Park

(57)          ABSTRACT

A tube-shaped implant insertion device may comprise: a needle having an internal space to accommodate a tube-shaped implant inserted into an eyeball; a handle connected to the needle to manipulate the position of the needle; and a guide pin disposed to support the implant accommodated in the needle, and having a hollow size smaller than the outer diameter of the implant. When using the tube-shaped implant insertion device, a tube-shaped implant is inserted into an eyeball by supporting same by means of a hollow guide pin and, after insertion, the needle is retracted by using a handle, and thus, there is an advantage in that an implant with an internally inserted wick can be easily inserted into the eyeball while not being separated from a suture.

11 Claims, 26 Drawing Sheets

(51) Int. Cl.
  *A61B 90/00* (2016.01)
  *A61F 2/14* (2006.01)
  *A61F 9/00* (2006.01)

(58) Field of Classification Search
  USPC ............................................................ 606/8
  See application file for complete search history.

(56)                    References Cited

U.S. PATENT DOCUMENTS

| | | |
|---|---|---|
| 9,592,151 B2 | 3/2017 | Rangel-Friedman et al. |
| 2011/0009874 A1 | 1/2011 | Wardle et al. |
| 2012/0197175 A1* | 8/2012 | Horvath .................. A61L 31/16 |
| | | 604/8 |

FOREIGN PATENT DOCUMENTS

| | | |
|---|---|---|
| JP | 2012532700 A | 12/2012 |
| KR | 102390116 B1 | 4/2022 |
| KR | 10-2022-0077178 A | 6/2022 |
| WO | 2022011321 A1 | 1/2022 |

* cited by examiner

APPARATUS FOR INJECTING TUBE-TYPE IMPLANT INTO EYE

TECHNICAL FIELD

Embodiments relate to an insertion device for a tube-type implant, and more particularly, to an insertion device that may easily insert an implant having a tube shape into an eyeball such as a tube for lowering intraocular pressure by draining aqueous humor in the eyeball and may minimize damage to the eyeball.

BACKGROUND

For a glaucoma patient whose intraocular pressure is not controlled even by using an intraocular pressure lowering agent, intraocular pressure is lowered by creating a bypass to drain aqueous humor from the anterior chamber of an eye to an external surface of the eye under the conjunctiva. Trabeculectomy among glaucoma filtration surgeries that create a bypass or a fistula for aqueous humor drainage may fail to control intraocular pressure when the amount of aqueous humor drainage decreases due to closure of the bypass after surgery. When initial surgery fails and glaucoma filtration surgery is performed again, the frequency of bypass closure after surgery increases and a success rate of surgery is low.

Also, even in the case of intractable glaucoma such as neovascular glaucoma or secondary glaucoma caused by uveitis according to types of glaucoma, closure of a bypass frequently occurs after trabeculectomy, resulting in poor results. For an eye with a history of failed glaucoma filtration surgery or intractable glaucoma, glaucoma implant surgery of locating a glaucoma implant device is performed to prevent closure of a bypass and increase a success rate of surgery. To date, glaucoma implant surgery has been used as an alternative to trabeculectomy, especially in several difficult-to-treat glaucoma, in that glaucoma implant surgery not only effectively lowers intraocular pressure but also shows a predictable postoperative clinical course according to an inner diameter of a given tube.

However, an existing glaucoma implant used for glaucoma implant surgery may cause various problems and complications such as difficulty in surgery due to a relatively large size, postoperative exposure, infection, eye movement disorder due to a large body, and diplopia. Accordingly, minimally-invasive glaucoma surgery (MIGS) using small-sized glaucoma implant instruments has recently been developed to relatively easily lower intraocular pressure by using a glaucoma implant and to reduce side effects after surgery due to a large size.

Surgery using a small-sized glaucoma implant has an advantage in that surgery may be completed by simply inserting a small-sized glaucoma implant under the conjunctiva into the anterior chamber of an eyeball. However, in order for aqueous humor to be drained from the eyeball at an appropriate pressure, a glaucoma implant with a very small size should be inserted and fixed at an appropriate position within the eyeball.

A conventional implant insertion device operates by inserting an implant itself into an insertion tube of the insertion device, inserting the insertion device into an eyeball, and then pushing the implant out into the eyeball.

However, this conventional method has a problem in that because the implant itself is pushed from the back to the front, it is difficult to insert the implant into the eyeball when another member such as a ripcord is coupled inside the implant. Also, this conventional method has a problem in that because the entire implant has to be inserted into the insertion tube, it is difficult to apply the conventional method to implants of various lengths. Furthermore, the conventional insertion device has a problem in that because a means for easily fixing positions of a needle of the insertion device and the implant inserted into the needle is not provided, the needle is unintentionally retracted during a process of inserting the needle of the insertion device into the eyeball, which easily exposes the implant.

SUMMARY

Technical Problem

To solve the problems described above, the present disclosure may provide an insertion device for a tube-type implant, which may insert an implant having a tube shape accommodated in a needle of the insertion device into an eyeball while being supported by a hollow guide pin and may retract the needle and/or the guide pin by using a handle after insertion so that the implant in which a ripcord is inserted is easily inserted into the eyeball without being separated from the ripcord.

Technical Solution

An insertion device for a tube-type implant according to an embodiment comprises: a needle having an inner space for accommodating an implant having a tube shape for insertion into an eyeball; a handle connected to the needle for manipulation of a position of the needle; and a guide pin disposed to support the implant accommodated in the needle and having a hollow portion smaller than an outer diameter of the implant.

According to an embodiment, the implant further comprises a ripcord inserted into the implant. Herein, the hollow portion of the guide pin is formed so that the ripcord is inserted into the hollow portion, and the insertion device for a tube-type implant further comprises a support rod at least partially disposed in the guide pin to support the ripcord.

The insertion device for a tube-type implant according to an embodiment further comprises: a handle body connecting the needle to the handle; and a housing in which the needle, the handle body, and the guide pin are accommodated, the housing comprising an opening extending in one direction, wherein the handle is exposed to outside through the opening of the housing and is configured to be slidable along the opening.

The insertion device for a tube-type implant according to an embodiment further comprises a feed adjustment unit coupled to one end of the housing and the guide pin to adjust a relative position of the guide pin with respect to the needle.

According to an embodiment, the opening comprises a first portion extending in a first direction, and a second portion connected to the first portion from a second direction different from the first direction to limit movement of the handle along the first direction, wherein the handle body is disposed in the housing to be movable in the first direction and rotatable in the second direction.

The insertion device for a tube-type implant according to an embodiment further comprises a stopper formed at an end of the housing to limit movement of the housing into an eyeball.

According to an embodiment, the stopper has a diameter greater than a diameter of the needle.

According to an embodiment, the needle is coupled to the handle to selectively expose the implant to outside of the needle by sliding along an outer surface of the guide pin through manipulation of the handle.

The insertion device for a tube-type implant according to an embodiment further comprises a piston coupled to the guide pin and disposed in the housing to selectively contact the handle body through manipulation of the handle.

The insertion device for a tube-type implant according to an embodiment further comprises a pipe coupled to the housing and connected to the piston; and a packing member disposed between the piston and the pipe.

According to an embodiment, the packing member is configured to allow relative movement of the piston with respect to the pipe through manipulation of the handle, in a state where the handle body is in contact with the piston.

The insertion device for a tube-type implant according to an embodiment further comprises one or more markers formed on a surface of the needle.

Advantageous Effects

According to an insertion device for a tube-type implant according to an embodiment of the present disclosure, when an implant having a tube shape such as an implant for eye disease for draining aqueous humor from the anterior chamber of an eyeball is inserted into the eyeball, because the implant is inserted into the eyeball while being supported by a hollow guide pin and a needle and/or the guide pin is retracted by using a handle after insertion, the implant in which a ripcord is inserted may be easily inserted into the eyeball without being separated from the ripcord.

Also, according to the insertion device for a tube-type implant according to an embodiment of the present disclosure, because a position of each portion may be adjusted through the needle, the guide pin, and a feed adjustment unit constituting the insertion device, the insertion device may be used with implants of various lengths. Furthermore, because a position of the needle may be fixed by rotating the handle for manipulating the needle along an opening formed in a surface of the insertion device, the needle may be prevented from being unintentionally retracted to expose the implant during a process of inserting the needle into the eyeball.

DETAILED DESCRIPTION OF EXEMPLARY EMBODIMENTS

Figure 1:
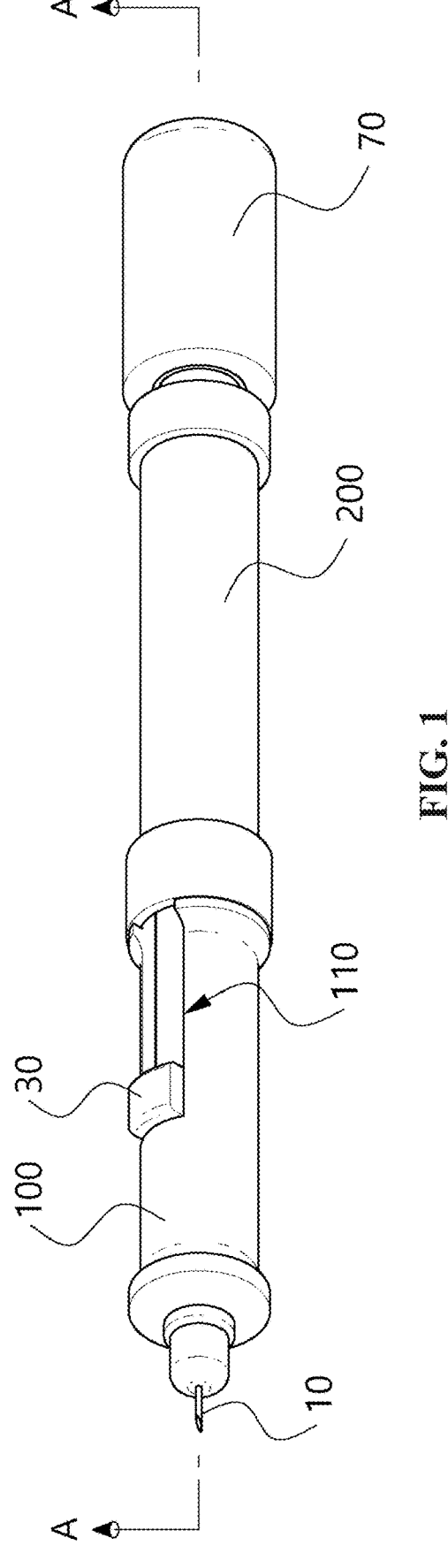
FIG. 1 is a view illustrating an insertion device for a tube-type implant according to an embodiment of the present disclosure.

The terms used herein will be briefly described, and the present disclosure will be described in detail.

The terms used herein are general terms currently widely used in the art in consideration of functions in the present disclosure, but the terms may vary according to the intention of one of ordinary skill in the art, precedents, or new technology in the art. Also, some of the terms used herein may be arbitrarily chosen by the present applicant, and in this case, these terms are defined in detail below. Accordingly, the specific terms used herein should be defined based on the unique meanings thereof and the whole context of the present disclosure.

It will be understood that when a certain part "includes" a certain component, the part does not exclude another component but may further include another component, unless the context clearly dictates otherwise. Also, throughout the specification, when an element is referred to as being "connected" to another element, it will be understood to include that the element is "directly connected" to the other element or is "connected" to the other element with another element therebetween.

The present disclosure will now be described more fully with reference to the accompanying drawings for one of ordinary skill in the art to be able to perform the present disclosure without any difficulty. However, the present disclosure may be embodied in many different forms and is not limited to the embodiments set forth herein. For clarity, portions irrelevant to the descriptions of the present disclosure are omitted in the drawings, and like components are denoted by like reference numerals throughout the specification.

An insertion device for a tube-type implant according to embodiments of the present disclosure is used to insert a tube-type implant into an eyeball. In this case, the tube-type implant refers to an implant having a tube shape substantially extending in a longitudinal direction and having an inner hollow portion or an implant including such a tube as at least one of its components.

In the specification, it is described that the implant insertion device according to embodiments is applied to insert an implant for eye disease for controlling intraocular pressure by controlling the drainage amount of aqueous humor generated in an anterior chamber located in front of a crystalline lens in the eyeball. Such an implant may prevent damage to an optic nerve due to increased intraocular pressure caused by eye diseases, and may be used to treat or alleviate symptoms of various eye diseases that cause or are caused by increased intraocular pressure. However, types of implants that may be used together with the implant insertion device according to embodiments are not limited thereto.

Eye diseases in the specification may include glaucoma caused by an increase in intraocular pressure. Examples of glaucoma may include, but are not limited to, congenital glaucoma, traumatic glaucoma, glaucoma suspect, ocular hypertension, primary open-angle glaucoma, normal-tension glaucoma, capsular glaucoma with pseudoexfoliation of lens, chronic simple glaucoma, low-tension glaucoma, pigmentary glaucoma, primary angle-closure glaucoma, acute angle-closure glaucoma, chronic angle-closure glaucoma, intermittent angle-closure glaucoma, glaucoma secondary to eye trauma, glaucoma secondary to eye inflammation, glaucoma secondary to drugs, neovascular glaucoma, and secondary glaucoma due to uveitis.

The implant for eye disease may be provided in a tube shape applicable to minimally-invasive glaucoma surgery (MIGS), and one end of the tube may be inserted into the anterior chamber of the eyeball and the other end of the tube is inserted into conjunctival tissue or Tenon's tissue. In various embodiments of the present disclosure, a planar shape of the tube-shaped implant may be any of various shapes such as a straight shape, a wedge shape, a cross shape, or a cover shape.

The implant for eye disease may be inserted after an operator exfoliates the conjunctival tissue or Tenon's tissue of the eyeball, and after insertion, the implant may be placed in the eyeball by covering the conjunctival tissue or Tenon's tissue again. Before the implant is inserted into the eyeball by using the insertion device according to embodiments, the operator may open a conjunctiva around a corneal limbus with surgical scissors or may create a scleral flap according to a condition of a sclera. Here, the scleral flap may have a substantially quadrangular or trapezoidal shape with a size of about 3 mm in width and length and may have a depth of about +50% of a thickness of the sclera, but the present disclosure is not limited thereto.

Next, a part of the implant may be inserted into the anterior chamber of the eyeball by injecting the implant for eye disease into the eyeball through the insertion device according to embodiments. The operator may insert a needle into the eyeball in a state where the implant is inserted (loaded) into the needle. For example, the operator may push the needle to a position at least 1 to 2 mm away from the corneal limbus. In this case, the implant inserted into the front of the needle may be located as far away from a cornea as possible. Next, the operator may withdraw the insertion device by using a handle of the insertion device so that only the implant remains in the eyeball.

A configuration of the insertion device for a tube-type implant according to embodiments for the above operation will be described in detail with reference to the attached drawings.

FIG. 1 is a view illustrating an insertion device for a tube-type implant according to an embodiment of the present disclosure.

Referring to FIG. 1, the insertion device for a tube-type implant may include a needle 10 having an inner space. Also, the insertion device may include a handle 30 connected to the needle 10 to enable manipulation of a position of the needle 10. Furthermore, the insertion device may include one or more housings 100, 200 forming an outer surface of the insertion device so that an operator holds the insertion device, while receiving the needle 10 and the handle 300 therein. For example, the housings may include a first housing 100 forming a front end of the insertion device and a second housing 200 coupled to the first housing 100 and forming a rear end of the insertion device, but the present disclosure is not limited thereto.

In an embodiment, the handle 30 is exposed to the outside through an opening 110 formed in a surface of the housing 100. The handle 30 may move forward and backward in a longitudinal direction of the insertion device along the opening 110. An operator may manipulate a position of the needle 10 connected to the handle 30 through the inside of the housing 100 by sliding the handle 30 along the opening 110. The operator may insert the needle 10 into an eyeball by using the insertion device in a state where the handle 30 is advanced up to a front end of the opening 110 (i.e., toward a patient's eye), and in this state, may retract the needle 10 connected to the handle 30 by pulling the handle 30 backward (i.e., toward the operator) along the opening 110.

In an embodiment, the insertion device for a tube-type implant includes a feed adjustment unit 70 coupled to one end of the housing 200. The feed adjustment unit 70 is a portion manipulated by the operator to control a position of a guide pin accommodated in the housings 100, 200, and has a mechanism for converting forward and backward movement and/or rotation of the feed adjustment unit 70 into forward and backward movement of the guide pin. A relative position of the guide pin with respect to the needle 10 may be adjusted through the feed adjustment unit 70. Position adjustment using the feed adjustment unit 70 will be described below in detail.

The needle 10 is a portion for mounting an implant and inserting the implant into the eyeball and may be formed of stainless steel or another biocompatible material. Also, other elements of the insertion device such as the handle 30, the housings 100, 200, and the feed adjustment unit 70 may also be formed of stainless steel, or may be formed of medical plastic based on polycarbonate, polypropylene, polyethylene, or poly vinyl chloride, silicone, or silicone rubber.

Although not shown, in an example, the insertion device may further include a gear structure (not shown) for moving the needle 10 in the longitudinal direction of the insertion device. The gear structure may enable delicate needle control by allowing the needle 10 to be moved or rotated by a smaller amount than the amount of movement of the operator's hand (e.g., forward/backward movement or rotation of the handle 30). Also, although not shown, one or more markers may be formed on a surface of the needle so that the operator easily checks a position of the needle.

Figure 2A:
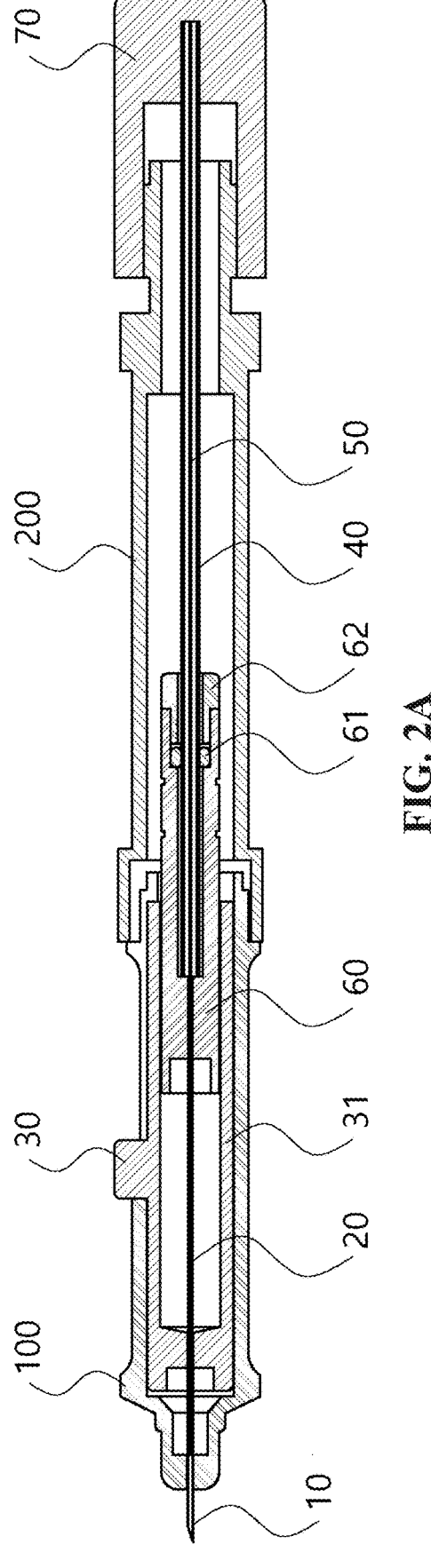
FIG. 2A is a cross-sectional view illustrating the insertion device for a tube-type implant of FIG. 1, taken along line A-A'.
Figure 2B:
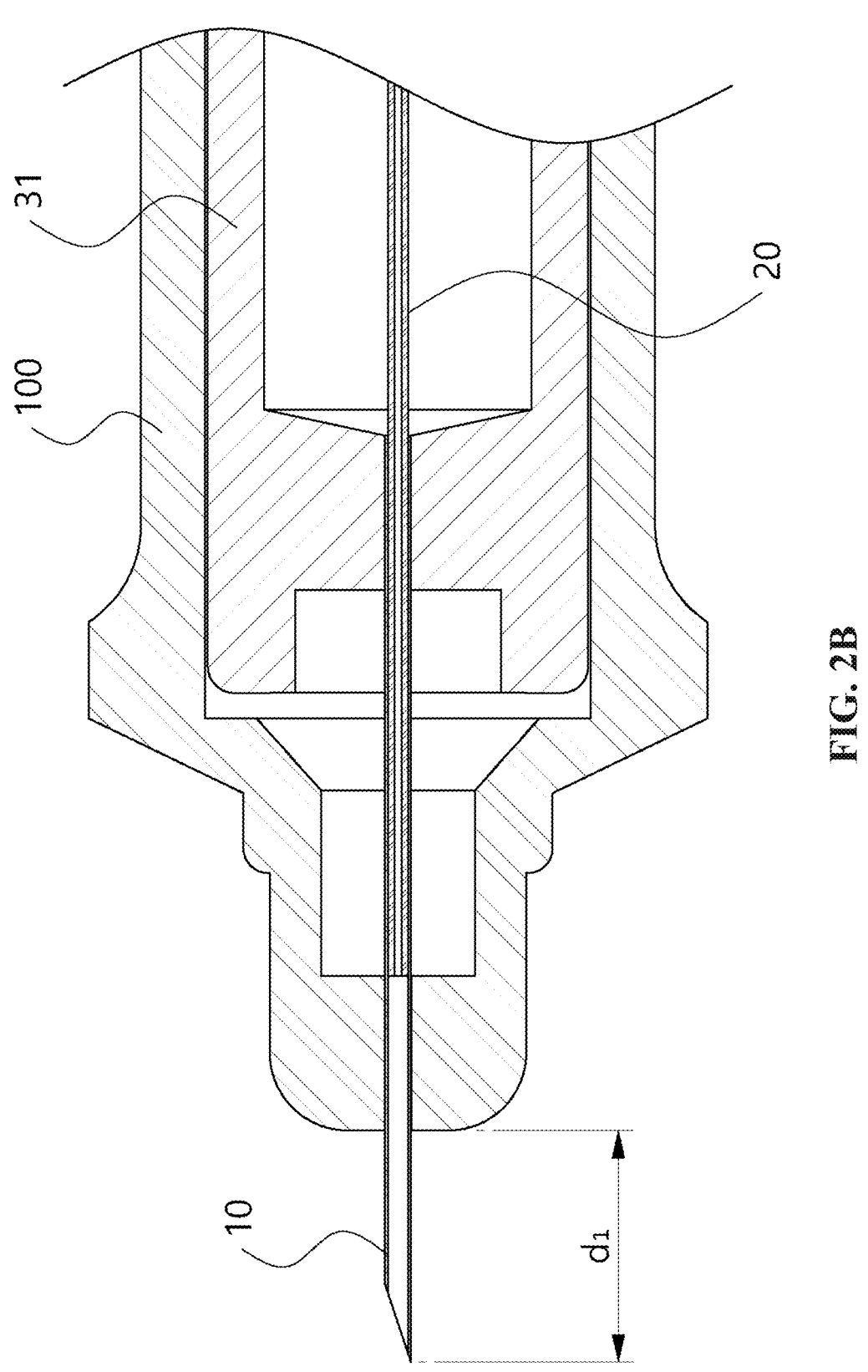
FIG. 2B is a partial cross-sectional view illustrating the insertion device for a tube-type implant of FIG. 2A.

FIG. 2A is a cross-sectional view illustrating the insertion device for a tube-type implant of FIG. 1, taken along line A-A'. FIG. 2B is a partial cross-sectional view illustrating the insertion device for a tube-type implant of FIG. 2A.

Referring to FIGS. 2A and 2B, the insertion device for a tube-type implant according to the present embodiment includes a guide pin 20 at least partially located in the needle 10 and supporting an implant to be inserted into an eyeball. The implant to be inserted into the eyeball is disposed in a space between a front end of the needle 10 and the guide pin 20. For insertion into the eyeball, the front end of the needle 10 may protrude forward by a certain length $d_1$ from a front end of the housing 100 of the insertion device. In this case, when an end of the needle 10 has an inclined shape, the length $d_1$ refers to a length including an inclined portion.

Because the guide pin 20 has a hollow portion therein but the hollow portion of the guide pin 20 is smaller than a size of the implant having a tube shape (i.e., an outer diameter of the tube) to be inserted into the needle 10, the implant is not inserted into the guide pin 20. Also, the hollow portion of the guide pin 20 should be larger than a diameter of a ripcord so that the ripcord coupled to the implant is inserted into the guide pin 20. The guide pin 20 may be formed of stainless steel or another biocompatible material, like the needle 10.

In the present embodiment, the handle 30 is connected to the needle 10 through a handle body 31 accommodated in the housing 100. Accordingly, forward and backward movement or rotation of the handle 30 may be transmitted to the needle 10 through the handle body 31. For example, the handle body 31 has a piston or pipe shape in which a front end of the handle body 31 is connected to the needle 10, and a knob protruding from an outer surface of the handle body 31 corresponds to the handle 30. The handle body 31 may also be formed of stainless steel, medical plastic, silicone, or the like, like the handle 30.

In an embodiment, the handle body 31 may have an at least partially hollow cylindrical shape, and is configured so that a piston 60 located behind the handle body 31 is inserted into the handle body 31. When the operator retracts the handle body 31 by manipulating the handle 30, an inner surface of the handle body 31 moves backward while an inner surface of the handle body 31 slides along an outer surface of the piston 60, and as a result, the needle 10 connected to the handle body 31 is retracted backward.

In an embodiment, a rear end of the piston 60 may be coupled to a pipe 40. The pipe 40 supports other members of the insertion device such as the needle 10, the handle body 31, and the piston 60 and fixes positions of the members so that they do not shake when the implant is inserted. In an embodiment, a rear end of the pipe 40 may be coupled to the feed adjustment unit 70, and the pipe 40 and the piston 60 coupled to the pipe 40 may be advanced or retracted as an operator moves the feed adjustment unit 70 forward and backward or rotates the feed adjustment unit 70. Also, a support rod 50 for supporting the ripcord of the implant may be located in the pipe 40.

In an embodiment, each of the piston 60 and the pipe 40 may be formed of stainless steel, medical plastic, silicone, or the like.

In an embodiment, a packing member 61 such as an O-ring may be located between the pipe 40 and the piston 60. For example, the rear end of the piston 60 surrounding an outer circumference of the pipe 40 may be blocked by a cap 62, and the packing member 61 may be located in a space between the cap 62 and the piston 60. The packing member 61 seals a space between the pipe 40 and the piston 60, but is formed of a flexible material that allows the piston 60 to move relative to the pipe 40 when the operator applies force to the handle 30 to retract the piston 60. The cap 62 prevents the packing member 61 from being separated from the piston 60 when the piston 60 moves in this way.

A process of inserting the implant by using the insertion device for a tube-type implant configured as described above will be described in detail.

Figure 3A:
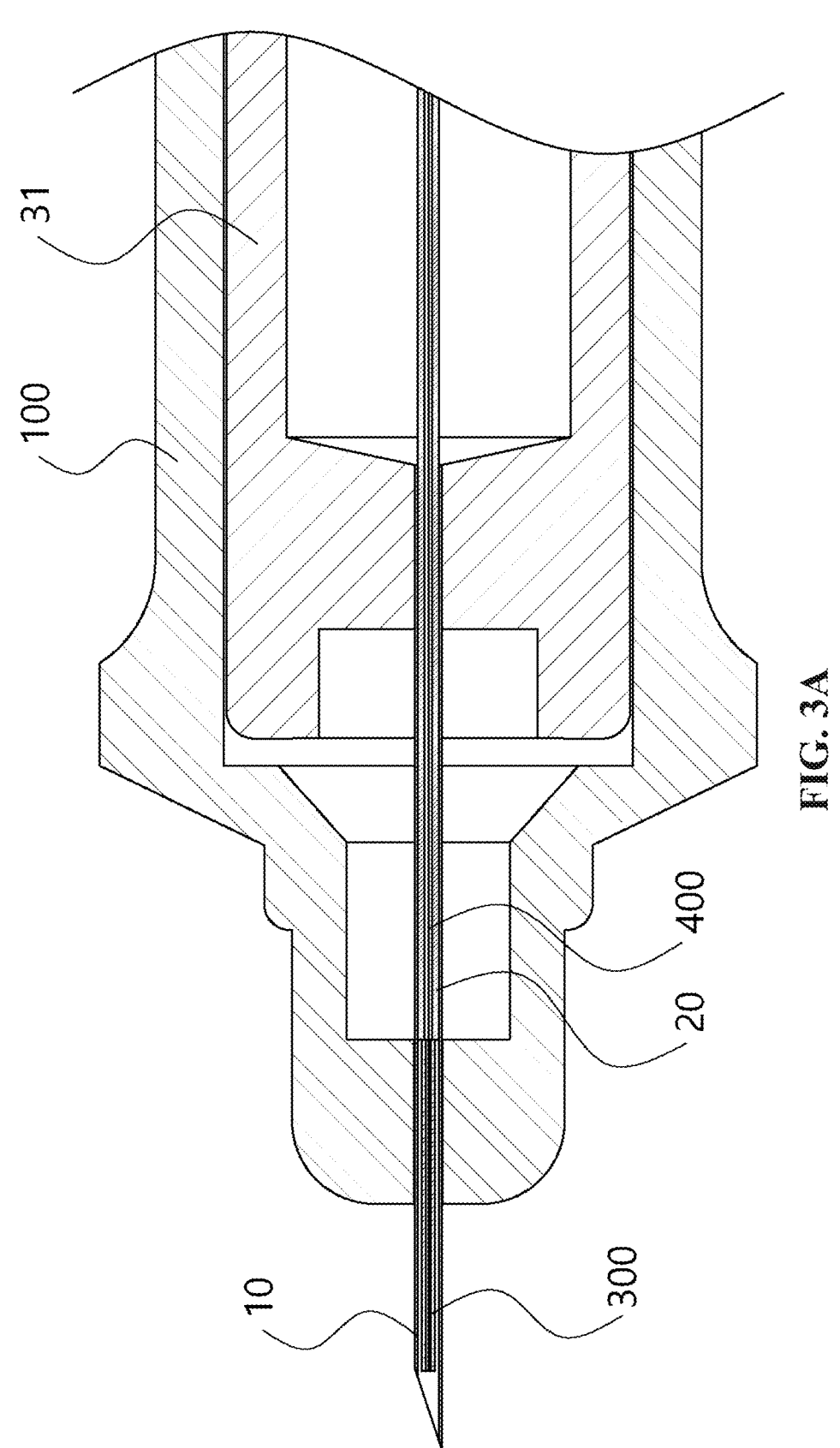
FIG. 3A is a view illustrating a state where an implant is mounted in an insertion device for a tube-type implant according to an embodiment of the present disclosure.

FIG. 3A is a view illustrating a state where an implant is mounted in an insertion device for a tube-type implant according to an embodiment of the present disclosure. Also, FIGS. 3B and 3C are a perspective view and a side view illustrating an arrangement of an implant and a guide pin in the state of FIG. 3A.

Figure 3B:
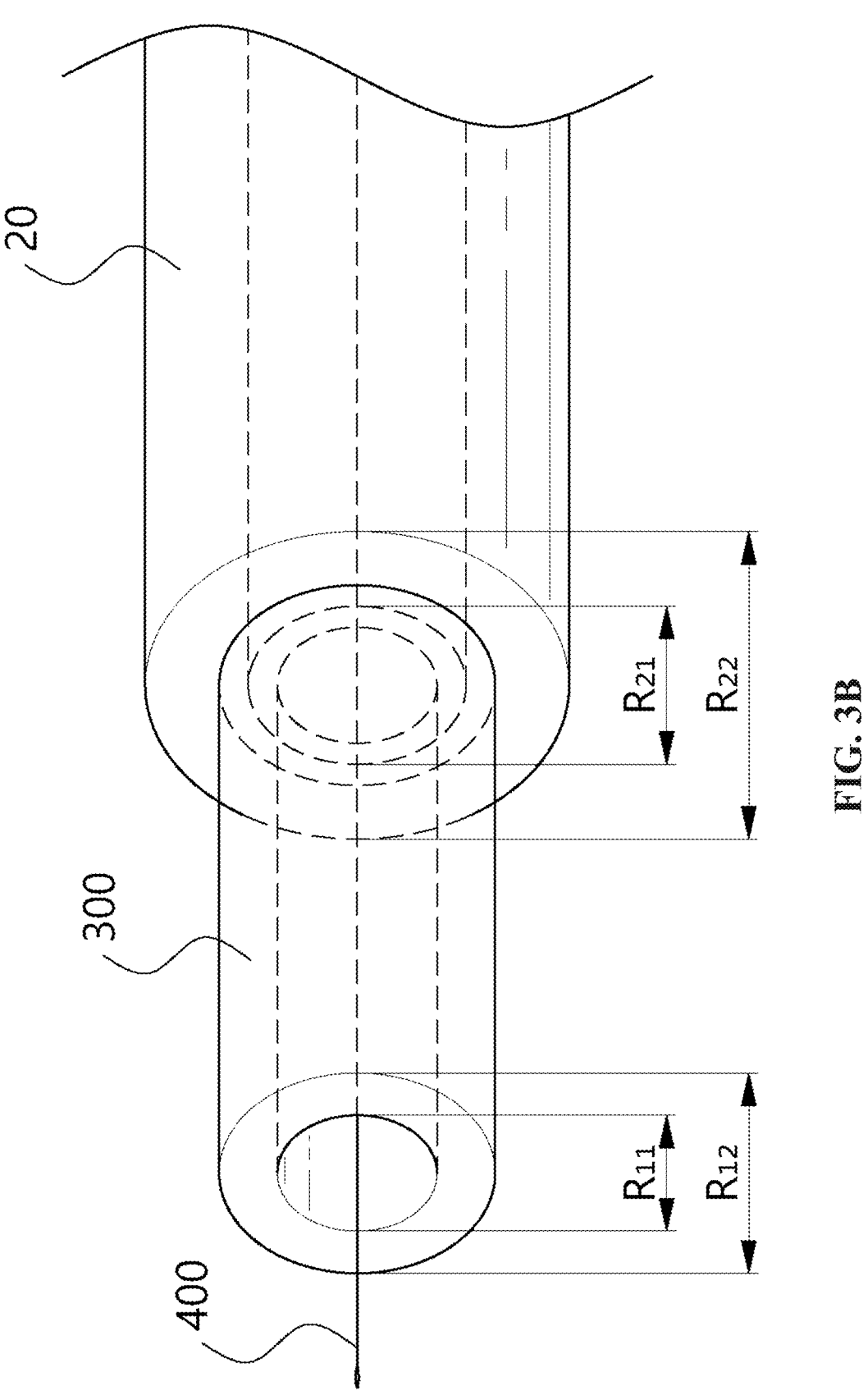
FIG. 3B is a perspective view illustrating an arrangement of an implant and a guide pin in an insertion device for a tube-type implant according to an embodiment of the present disclosure.
Figure 3C:
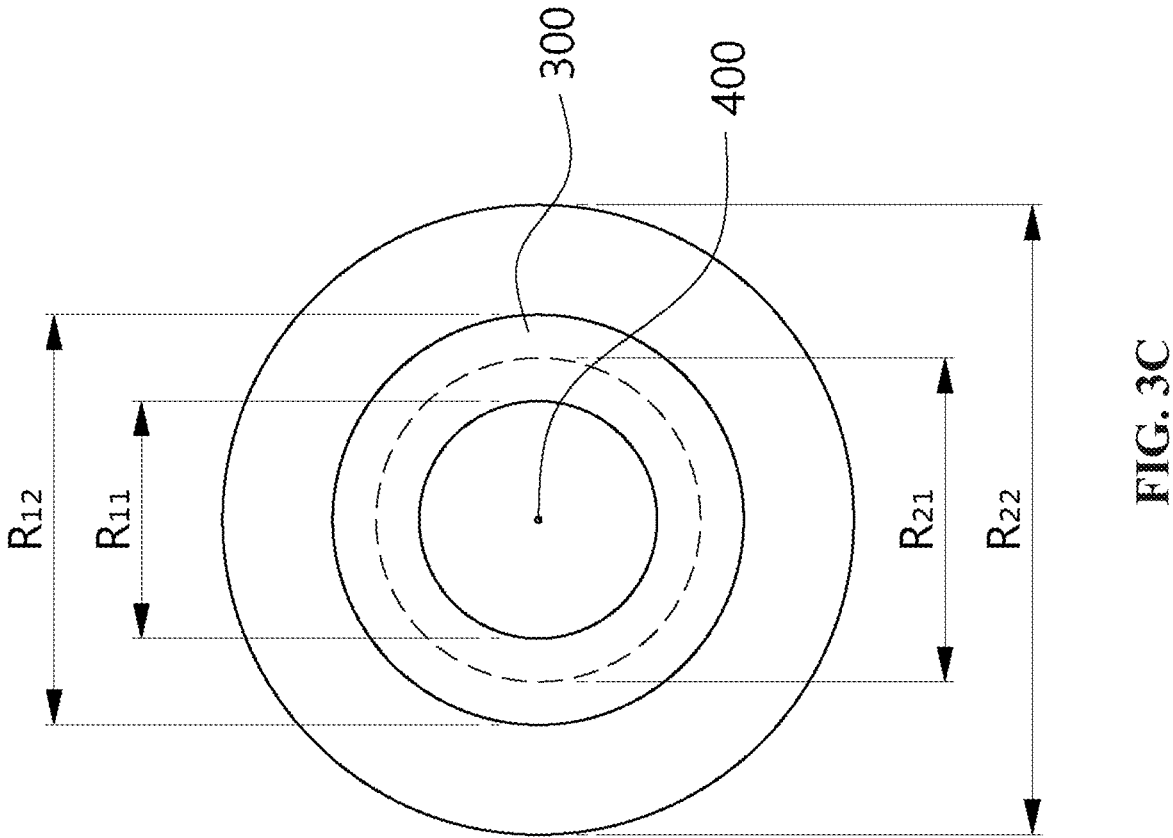
FIG. 3C is a side view illustrating an arrangement of an implant and a guide pin in an insertion device for a tube-type implant according to an embodiment of the present disclosure.

Referring to FIGS. 3A to 3C, an implant 300 to be inserted into an eyeball may be inserted into the needle 10 through a front end of the needle 10. An operator may prepare the insertion device according to embodiments, may insert the implant 300 into the insertion device, and may perform insertion into the eyeball. Also, the insertion device according to embodiments may be manufactured and packaged with the implant 300 at least partially inserted therein and may be delivered to the operator. The implant 300 includes a hollow portion therein in order to drain aqueous humor in the eyeball.

Also, a ripcord 400 for controlling a speed of aqueous humor drainage may be inserted into the hollow portion of the implant 300. The ripcord 400 may be a non-absorbable surgical suture thread, and may be formed of a nylon or prolene material, but the present disclosure is not limited thereto. The ripcord 400 is at least partially inserted into the hollow portion of the implant 300 to control pressure in an anterior chamber. When the ripcord 400 is thick, a space between an inner wall of the implant 300 and the ripcord 400 becomes narrow and aqueous humor is relatively slowly drained, and thus pressure in the anterior chamber increases. When the ripcord 400 is thin, a space between the inner wall of the implant 300 and the ripcord 400 becomes wide and aqueous humor is relatively rapidly drained, and thus, pressure in the anterior chamber decreases.

Accordingly, the ripcord 400 may be formed of a material with a diameter to optimize pressure in the anterior chamber to a certain range, for example, postoperative pressure to about 6 to 21 mmHg. However, a desirable numerical range of pressure in the anterior chamber is not limited thereto. Also, the ripcord 400 may be manipulated by a clinician to control pressure in the anterior chamber. For example, when the ripcord 400 is inserted into the hollow portion of the implant 300 and is exposed from a rear end of the implant 300, the clinician may control the amount of aqueous humor drainage by adjusting the ripcord 400 exposed from the rear end of the implant 300.

In an embodiment, the implant 300 may be formed of any one of silicone, polytetrafluoroethylene, polycarbonate, polyurethane, polyethylene, polypropylene, polyimide, poly (methyl methacrylate) (PMMA), poly(styrene-b-isobutylene-b-styrene), polyethersulfone, gelatin, stainless steel, titanium, and nitinol or a combination of one or more thereof, but the present disclosure is not limited thereto.

In an embodiment, the implant 300 may be formed in a curved shape with a certain curvature in order to prevent damage to the endothelium of a cornea in the eyeball. A front end of the implant may poke and damage the cornea in the anterior chamber of the eyeball in a process of inserting the implant into the anterior chamber of the eyeball according to a size of the eyeball that is different for each patient, a skill level in implant injection, etc. Damage to the cornea may cause complications such as corneal decompensation which require even future corneal transplantation. For example, in order for the implant to naturally move in a curved shape while being inserted into the anterior chamber of the eyeball, the implant may be manufactured in a curved shape with a certain curvature corresponding to a curvature of a surface of the eyeball. Alternatively, even a straight implant with no curvature may be used by using a material with sufficient elasticity or flexibility.

The implant 300 accommodated in the needle 10 is located between the front end of the needle 10 and the guide pin 20. The guide pin 20 supports the implant 300 and accommodates the ripcord 400 coupled to the implant 300 in a hollow portion of the guide pin 20. To this end, an inner diameter $R_{21}$ of the guide pin 20 should be large enough to allow the ripcord 400 to be inserted into the guide in 20, but the inner diameter $R_{21}$ of the guide pin 20 should be less than an outer diameter $R_{12}$ of the implant 300 so that the implant 300 is not pushed into the guide pin 20. For example, the inner diameter $R_{21}$ of the guide pin 20 may be between an inner diameter $R_{11}$ of the implant 300 and the outer diameter $R_{12}$ of the implant 300, but the present disclosure is not limited thereto. Also, an outer diameter $R_{22}$ of the guide pin 20 may be equal to or greater than the outer diameter $R_{12}$ of the tube, but the present disclosure is not limited thereto.

That is, the insertion device according to embodiments is configured so that the implant 300 having a tube shape is supported by the guide pin 20 which is another tube-shaped member. Because the implant 300 is supported by the guide pin 20 having the hollow portion, even when the ripcord 400 is coupled inside the implant 300, there is no need to force the ripcord 400 into the needle 10 in a bent or clumped state, and the implant 300 may be placed in the insertion device in a state where the ripcord 400 is inserted into the guide pin 20.

The insertion device according to embodiments is configured so that positions of the guide pin 20 and the support rod 50 connected to the feed adjustment unit 70 are adjusted by manipulating the feed adjustment unit 70. Because the implant 300 inserted into the eyeball is disposed between the front end of the needle 10 and the guide pin 20, a position of the guide pin 20 may be adjusted according to a length of the implant 300 in order to use the implants 300 of various lengths. At the same time, because a position of the support rod 50 supporting the ripcord 400 coupled to the implant 300 is also adjusted by manipulating the feed adjustment unit 70, a position of the support rod 50 may be appropriately adjusted according to a length of the ripcord 400 coupled to the implant 300.

When the implant 300 is placed in the insertion device, the operator may move the insertion device so that an end of the implant 300 is located at a desired insertion point in the eyeball. Also, the operator may insert the needle 10 into a portion where the implant 300 should be located in the eyeball, and then may manipulate the feed adjustment unit 70 to check a position of the implant 300. The guide pin 20 is advanced by manipulating the feed adjustment unit 70 to push the implant 300 forward.

Figure 4A:
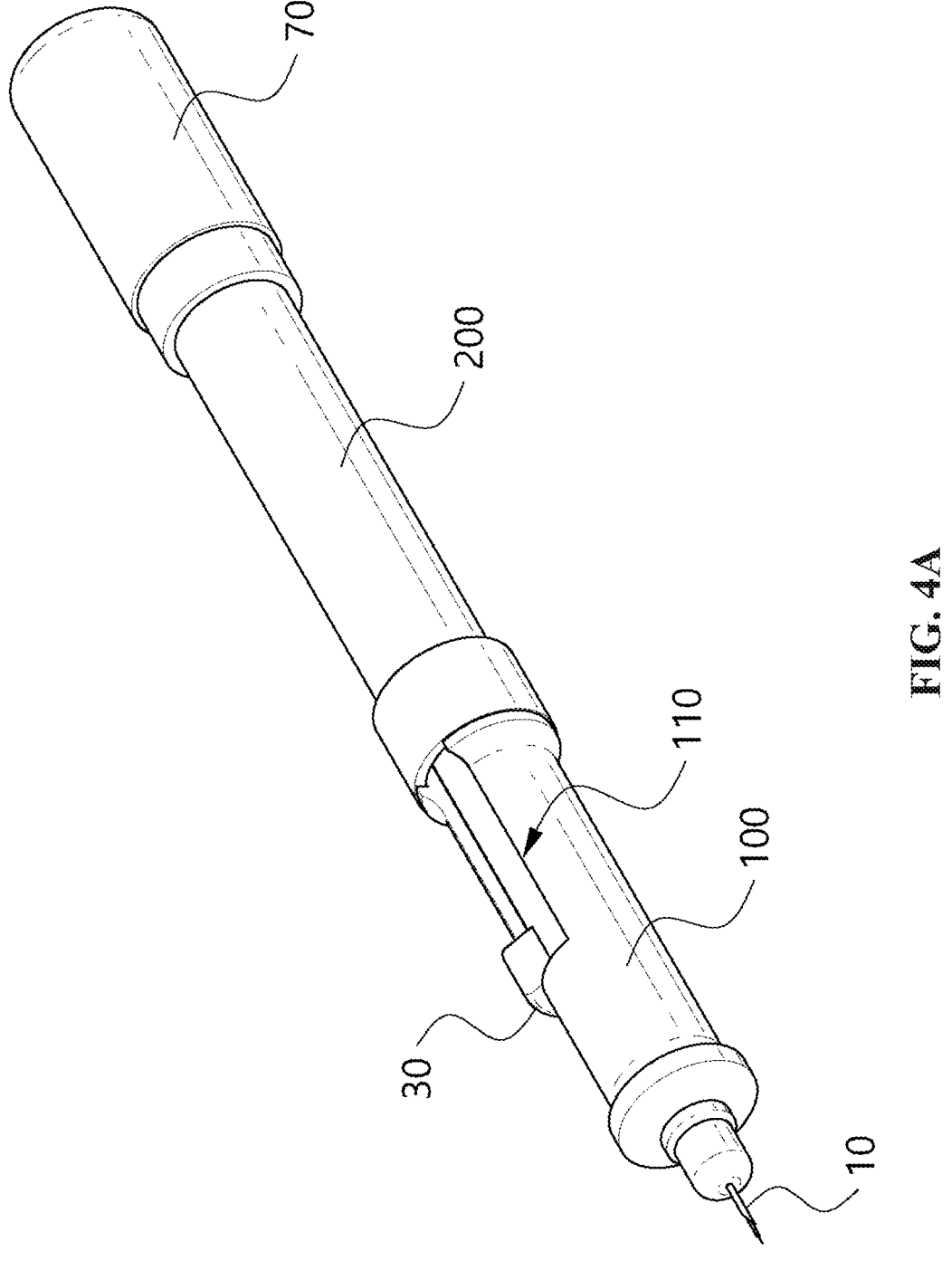
FIG. 4A is a view illustrating a state where a guide pin is advanced in an insertion device for a tube-type implant according to an embodiment of the present disclosure.
Figure 4B:
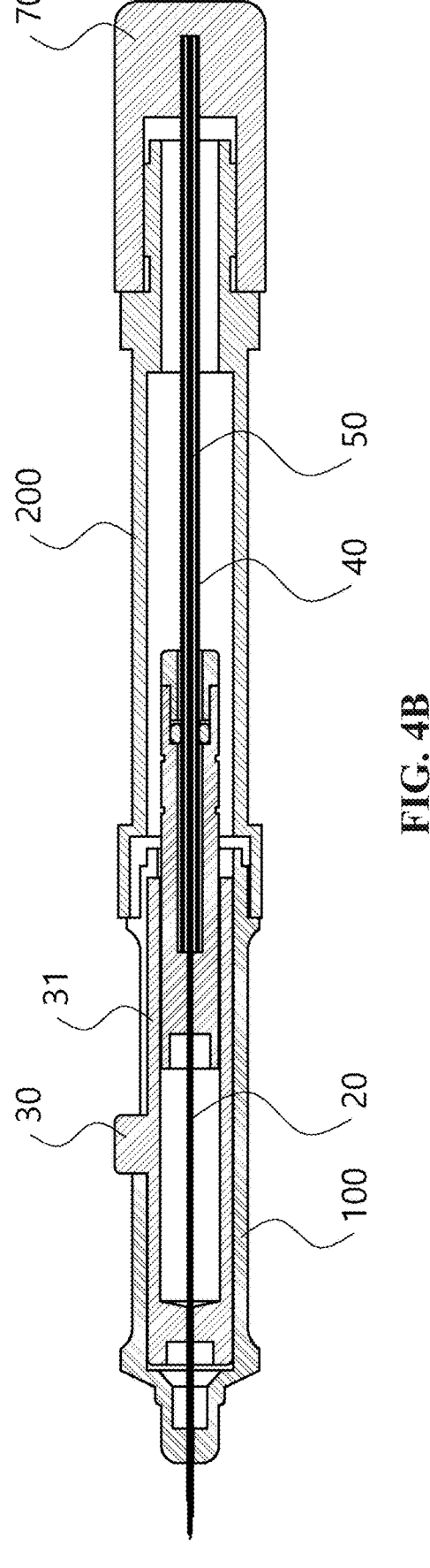
FIG. 4B is a cross-sectional view illustrating the insertion device for a tube-type implant of FIG. 4A.
Figure 4C:
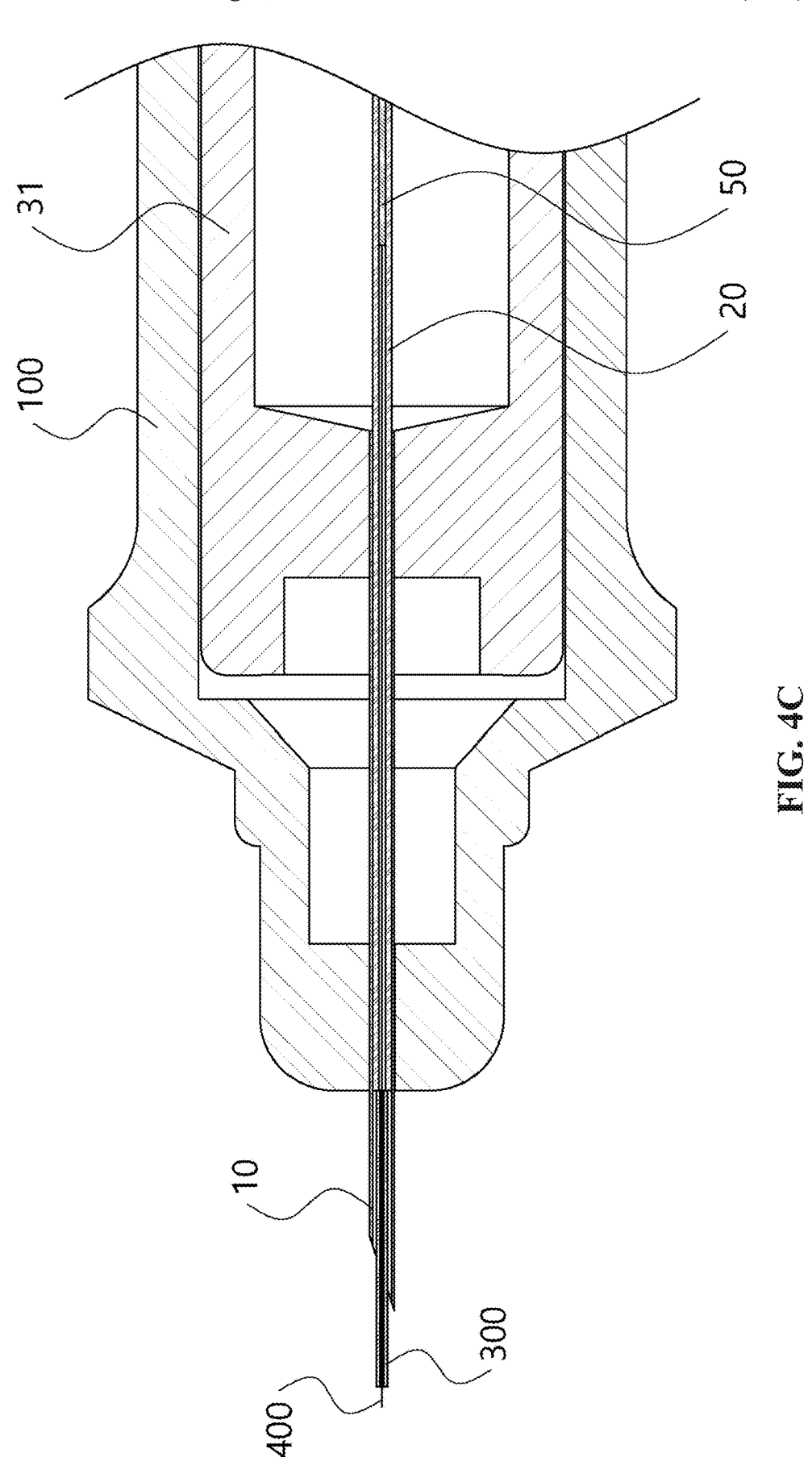
FIG. 4C is a partial cross-sectional view illustrating the insertion device for a tube-type implant of FIG. 4B.

FIG. 4A is a view illustrating a state where a guide pin is advanced in an insertion device for a tube-type implant according to an embodiment of the present disclosure. FIGS. 4B and 4C are cross-sectional views illustrating the insertion device for a tube-type implant of FIG. 4A.

Referring to FIGS. 4A to 4C, an operator may advance the guide pin 20 by using the feed adjustment unit 70 in a state where the implant 300 is disposed in the needle 10 as described with reference to FIG. 3A. In more detail, the feed adjustment unit 70 is coupled to the pipe 40, the pipe 40 is coupled to the piston 60, and the piston 60 is coupled to the guide pin 20. When the feed adjustment unit 70 is advanced until the feed adjustment unit 70 reaches the housing 200, the pipe 40, the piston 60, and the guide pin 20 connected to the feed adjustment unit 70 are advanced by that amount. When the feed adjustment unit 70 has a rotation mechanism, the insertion device may include a rotation gear (not shown) for converting rotation of the feed adjustment unit 70 into forward and backward movement of the pipe 40.

Because a rear side of the implant 300 is supported by the guide pin 20 so that the implant 300 is not pushed into the guide pin 20, when the guide pin 20 is advanced due to manipulation of the operator, only the implant 300 is advanced in a state where a position of the needle 10 is fixed. Accordingly, the operator may manipulate the feed adjustment unit 70 to the extent that the implant 300 is slightly exposed outside a front end of the needle 10 and a position of the implant 300 inserted into the needle 10 is checked.

In an embodiment, the support rod 50 disposed behind the guide pin 20 is moved forward or backward through manipulation of the feed adjustment unit 70 by the operator, like the pipe 40. Also, the support rod 50 is at least partially inserted into the guide pin 20 and supports the ripcord 400 coupled to the implant 300. When the operator pushes the guide pin 20 by manipulating the feed adjustment unit 70 to advance the implant 300, the support rod 50 pushes the ripcord 400 forward at the same time, thereby preventing only the implant 300 from being advanced while leaving the ripcord 400 inside the insertion device. The support rod 50 may be formed of stainless steel or another biocompatible material.

In a state where the implant 300 is inserted into an insertion position in an eyeball, the operator may retract the needle 10 by using the handle 30 of the insertion device so that only the implant 300 remains in the eye.

Figure 5A:
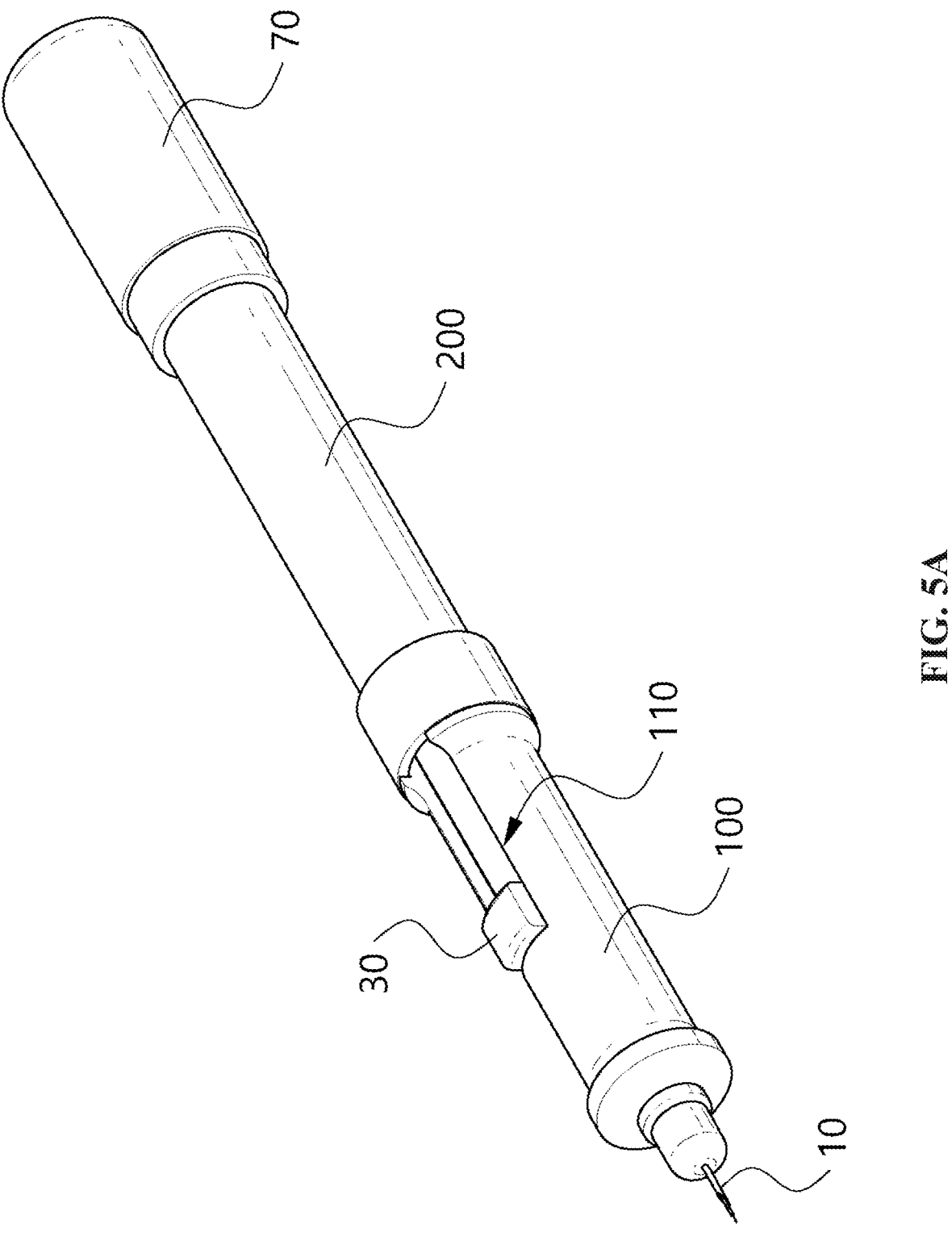
FIGS. 5A and 5B are views illustrating a state where a handle is rotated to a movable position in an insertion device for a tube-type implant according to an embodiment of the present disclosure.
Figure 5B:
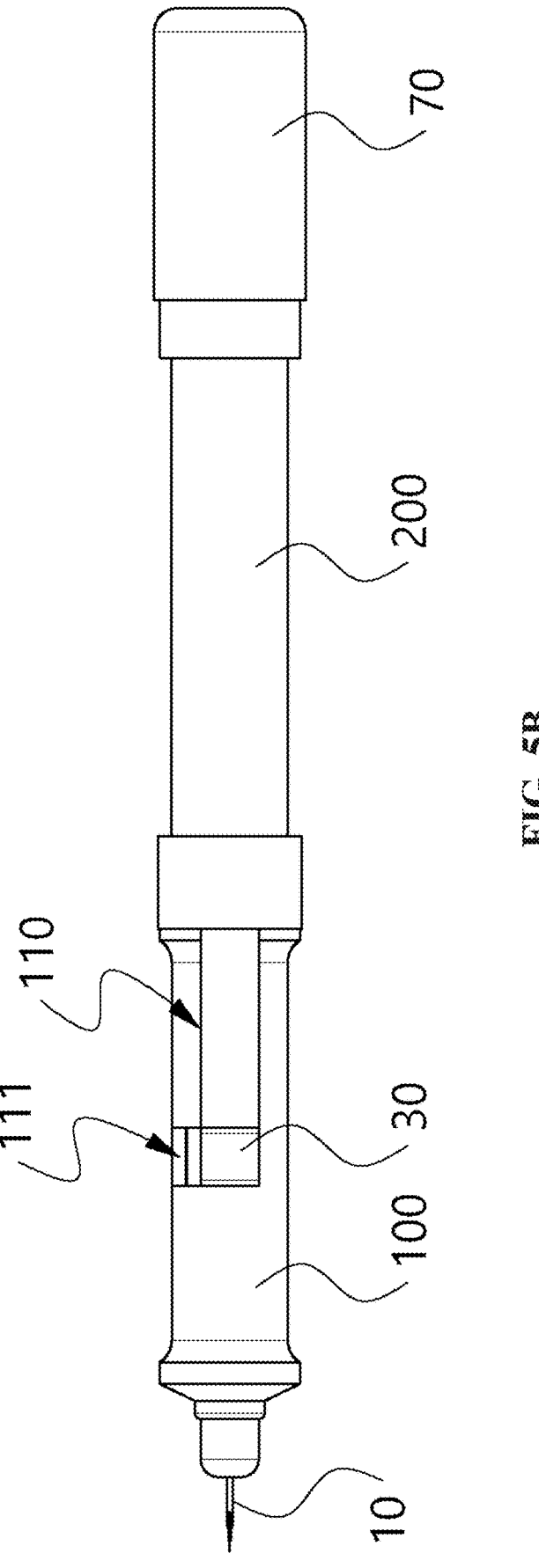
Figure 5C:
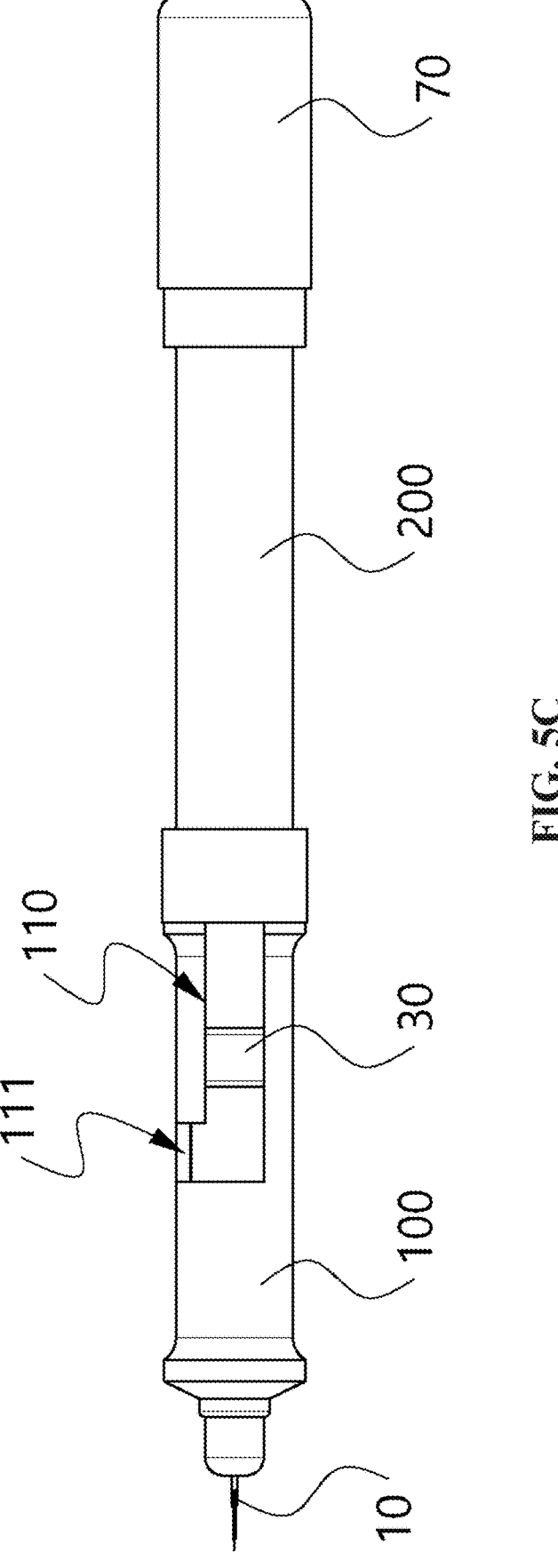
FIG. 5C is a view illustrating a state where a handle is retracted in the insertion device for a tube-type implant of FIG. 5B.

FIGS. 5A to 5C are views illustrating a process in which an operator retracts the needle 10 by using the handle 30 when the implant 300 is disposed at an insertion position.

Referring to FIGS. 5A and 5B, the opening 110 of the housing 110 for sliding the handle 30 may include a portion that is bent in a direction different from other portions in order to limit movement of the handle 30. That is, the opening 110 extends in a longitudinal direction of the insertion device and includes a groove 111 extending in a direction different from the longitudinal direction of the insertion device. Alternatively, when a portion of the opening 110 extending in the longitudinal direction is a first portion, a portion of the opening 110 extending in a direction different from the first portion is referred to as a second portion. For example, the opening 110 having the first portion and the second portion may have a shape such as "⌐", "⌐", "⊣", or "⊢".

The first portion of the opening 110 corresponds to a movable position at which the handle 30 may move, and the second portion corresponds to a fixed position at which the handle 30 may not move. The operator may insert the needle 10 into an eyeball in a state where the handle 30 is rotated to the fixed position so that the handle 30 is fixed and does not move forward and backward, and when the needle 10 is inserted to a desired position, the operator may rotate the handle 30 to the movable position as shown in FIGS. 5A and 5B. Next, the operator may retract the needle 10 backward along the longitudinal direction of the insertion device by sliding the handle 30 backward as shown in FIG. 5C.

When the operator wants to fix a position of the needle 10, the operator may advance the handle 30 to an end of the opening 110 and then may rotate the handle 30 so that the handle 30 is within the groove 111. Because forward and backward movement of the handle 30 is restricted in a state where the handle 30 is located in the groove 111, the needle 10 does not shake.

A conventional implant insertion device has a problem in that when a needle is inserted into an eyeball of a patient and then retracted, a lot of force is applied, which may strain the eyeball of the patient. However, because the implant insertion device according to embodiments may easily adjust a position of the needle 10 by sliding the handle 30 and may fix a position of the handle 30, the needle 10 may be prevented from being unintentionally retracted to expose the implant 300 in a process of inserting the needle 10 into the eyeball.

Figure 6A:
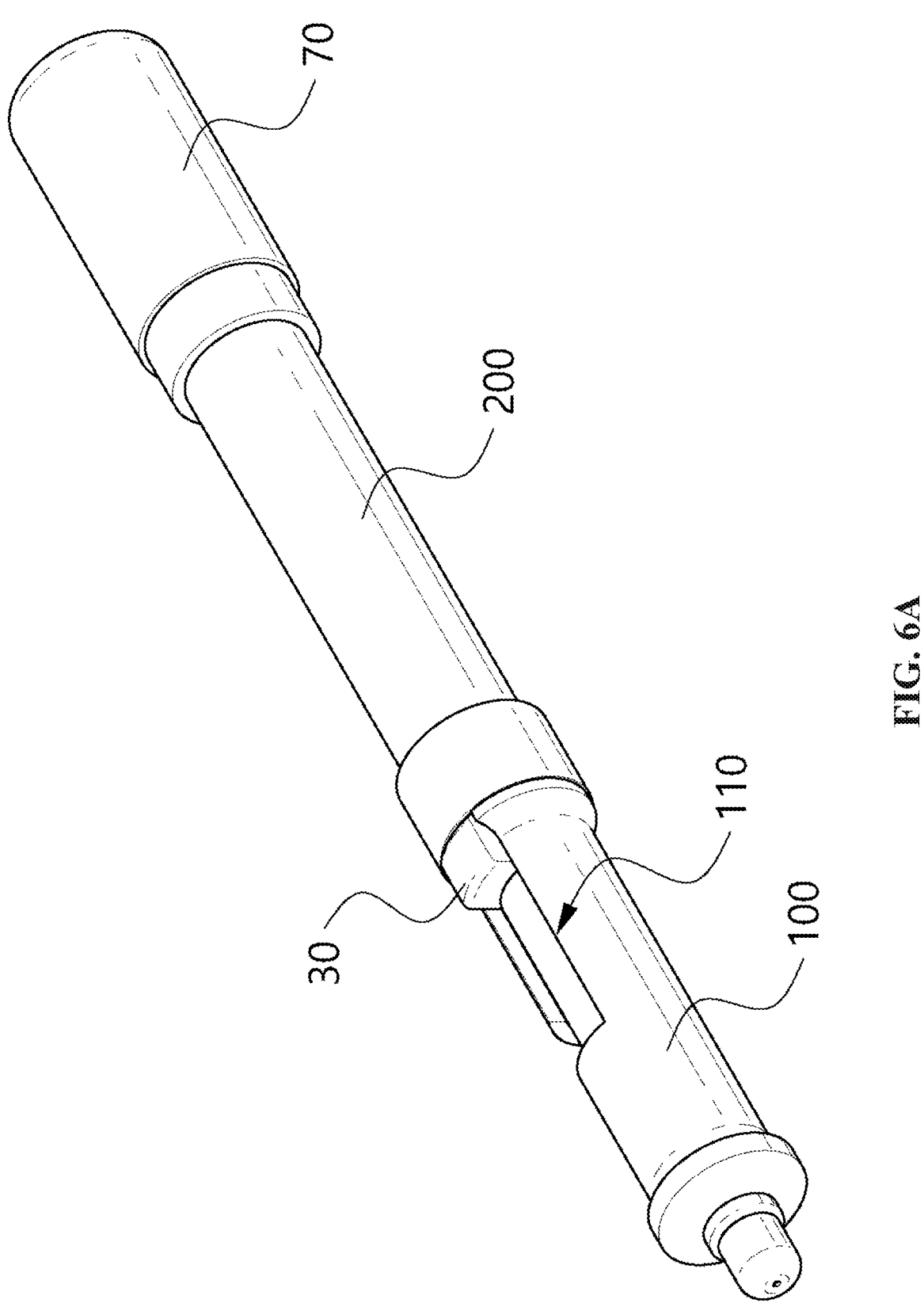
FIG. 6A is a view illustrating a state where a needle is retracted in an insertion device for a tube-type implant according to an embodiment of the present disclosure.
Figure 6B:
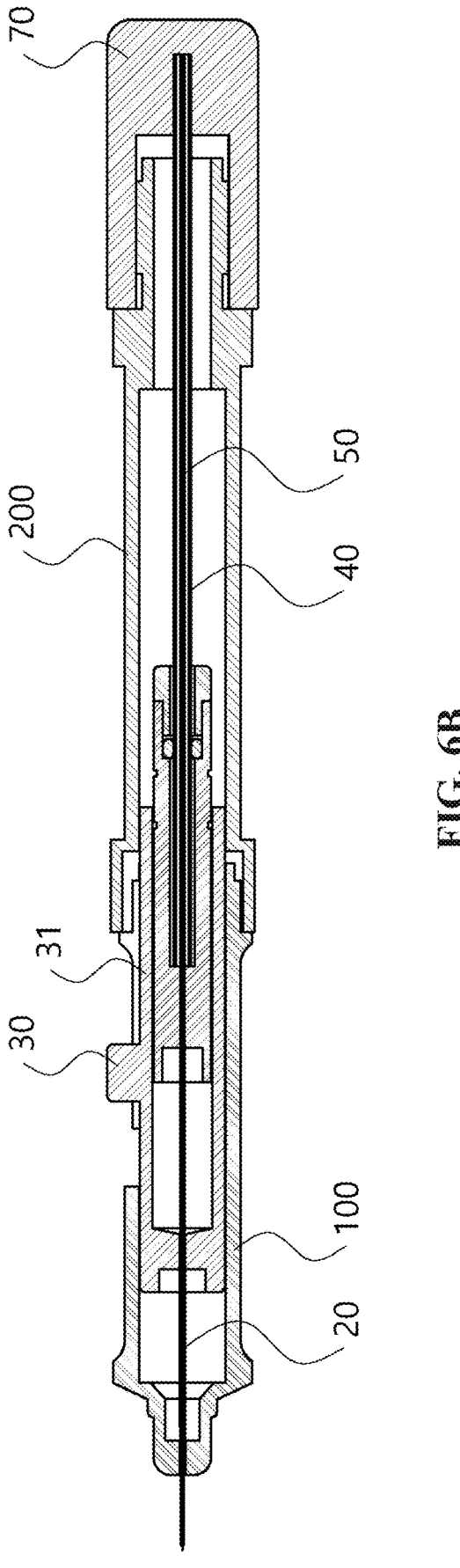
FIG. 6B is a cross-sectional view illustrating the insertion device for a tube-type implant of FIG. 6A.
Figure 6C:
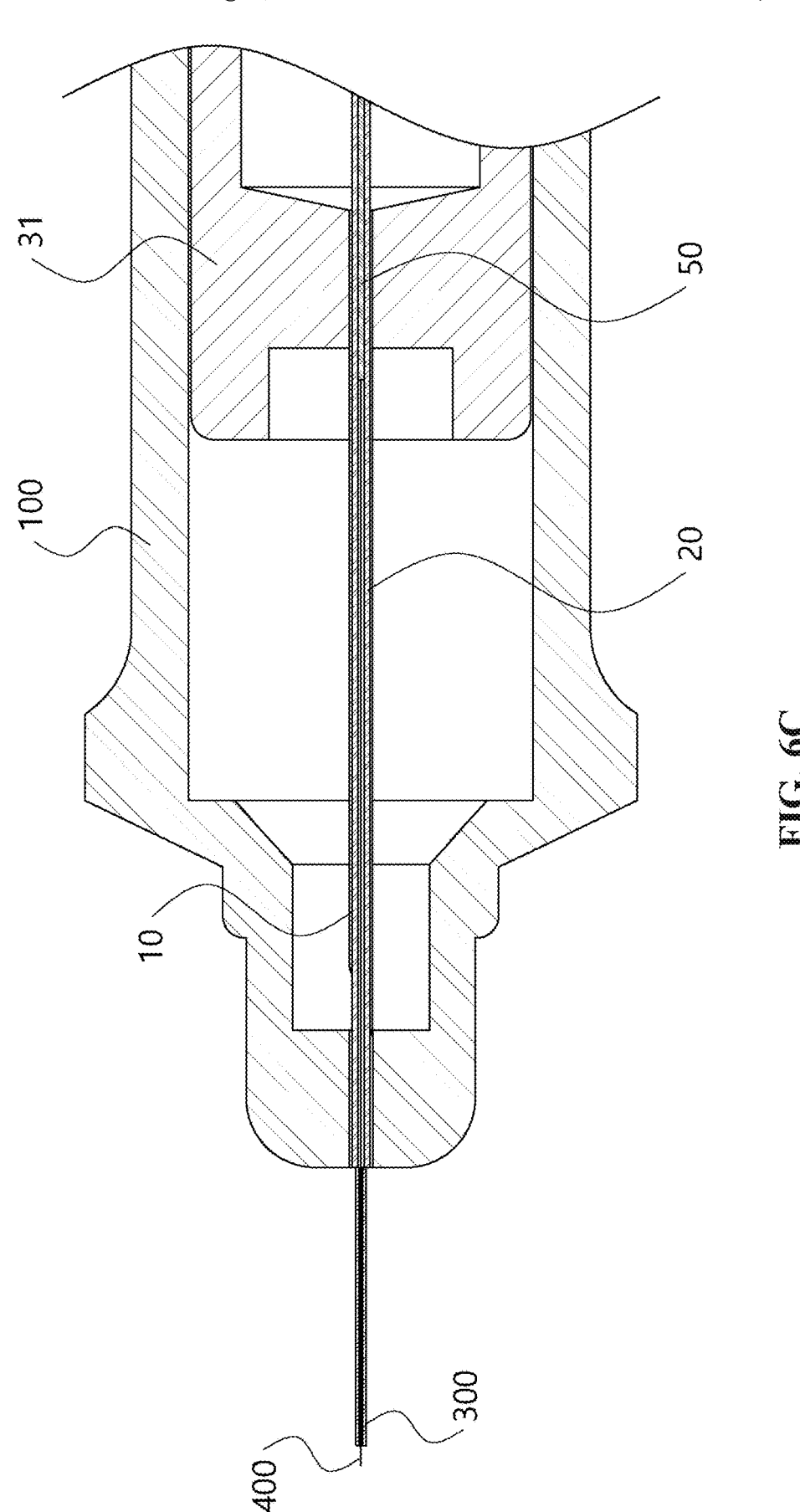
FIG. 6C is a partial cross-sectional view illustrating the insertion device for a tube-type implant of FIG. 6B.

FIG. 6A is a view illustrating a state where a needle is retracted in an insertion device for a tube-type implant according to an embodiment of the present disclosure. FIGS. 6B and 6C are cross-sectional views illustrating the insertion device for a tube-type implant of FIG. 6A.

Referring to FIGS. 6A to 6C, in a state where the implant 300 is inserted into an insertion position in an eyeball, the needle 10 may be retracted into the housing 100 by sliding the handle 30 along the opening 110. As a result, as shown in FIG. 6C, only the implant 300 remains outside the insertion device, and in this state, an operator may place the implant at a desired position in the eyeball by withdrawing the insertion device. The ripcord 400 inserted into the guide pin 20 of the insertion device is separated from the guide pin 20 while the operator withdraws the insertion device, and is located in the eyeball together with the implant 300.

The insertion device for a tube-type implant according to embodiments of the present disclosure as described above is configured to retract a needle while leaving an implant in an eyeball when the implant is inserted. However, an insertion device for a tube-type implant according to another embodiment may be configured to retract a needle and a guide pin together when an implant is inserted, which will be described below in detail.

Figure 7A:
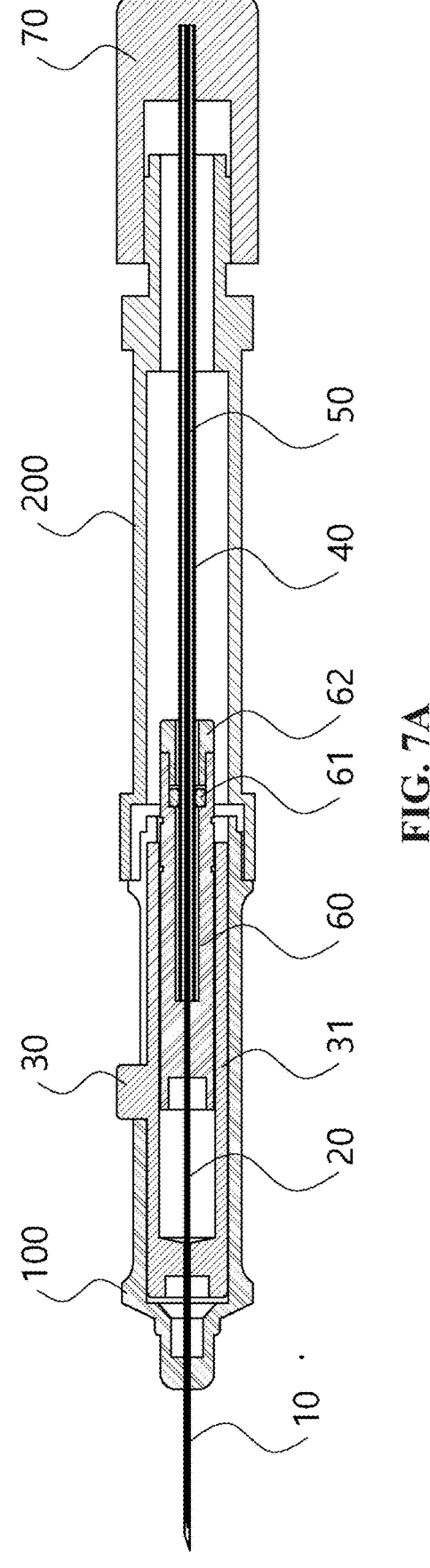
FIG. 7A is a view illustrating a state where an implant is mounted in an insertion device for a tube-type implant according to another embodiment of the present disclosure.
Figure 7B:
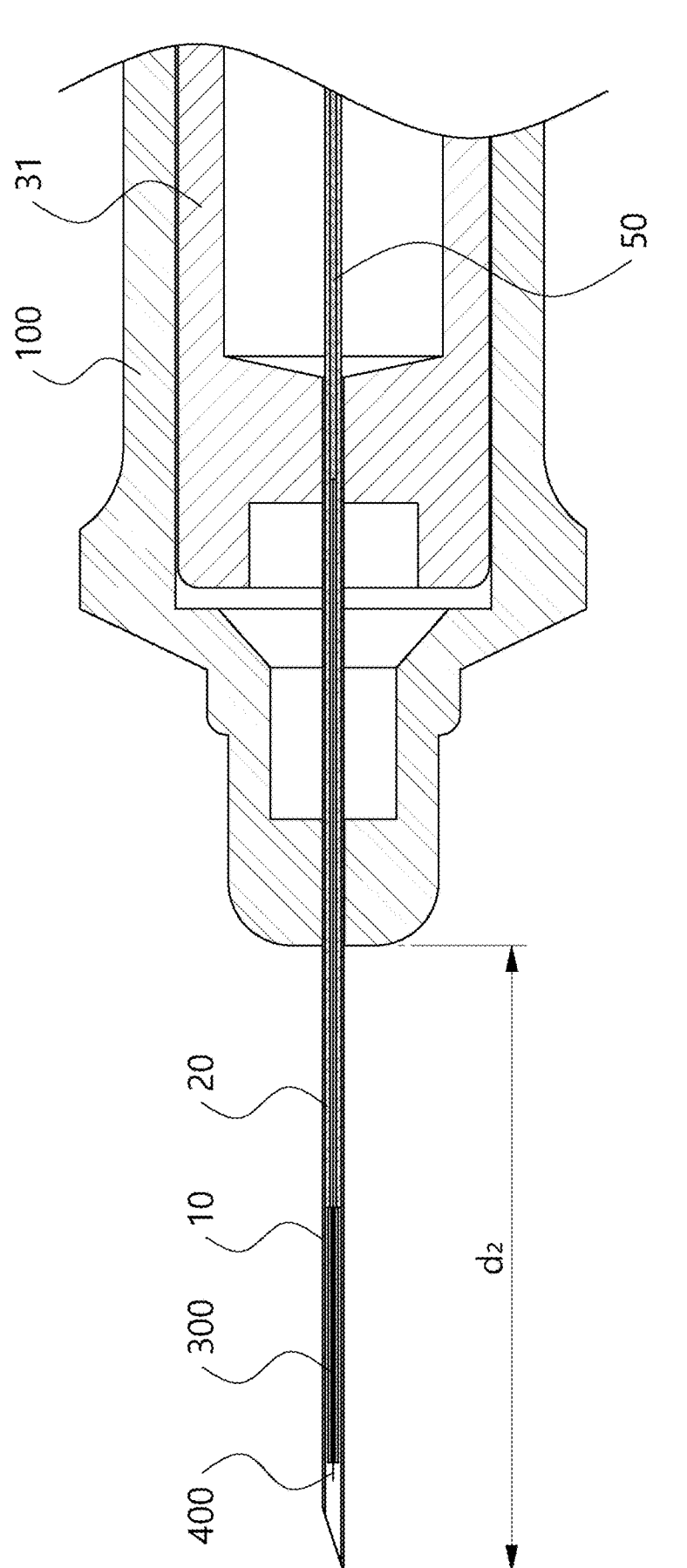
FIG. 7B is a partial cross-sectional view illustrating the insertion device for a tube-type implant of FIG. 7A.

FIG. 7A is a view illustrating a state where an implant is mounted in an insertion device for a tube-type implant according to another embodiment of the present disclosure. FIG. 7B is a partial cross-sectional view illustrating the insertion device for a tube-type implant of FIG. 7A.

Referring to FIGS. 7A and 7B, the implant 300 to be inserted into an eyeball may be inserted into the needle 10 through a front end of the needle 10. The implant 300 inserted into the needle 10 is disposed between the front end of the needle 10 and the guide pin 20. This arrangement is the same as that described with reference to FIGS. 3A to 3C, and thus, a detailed description thereof will be omitted to avoid repetition. However, in the insertion device configured so that both the needle 10 and the guide pin 20 are retracted, a length $d_2$ of the needle protruding from a front end of the housing 100 of the insertion device may be greater than the length $d_1$ of the needle 10 protruding in the insertion device configured so that only the needle 10 is retracted.

Figure 8A:
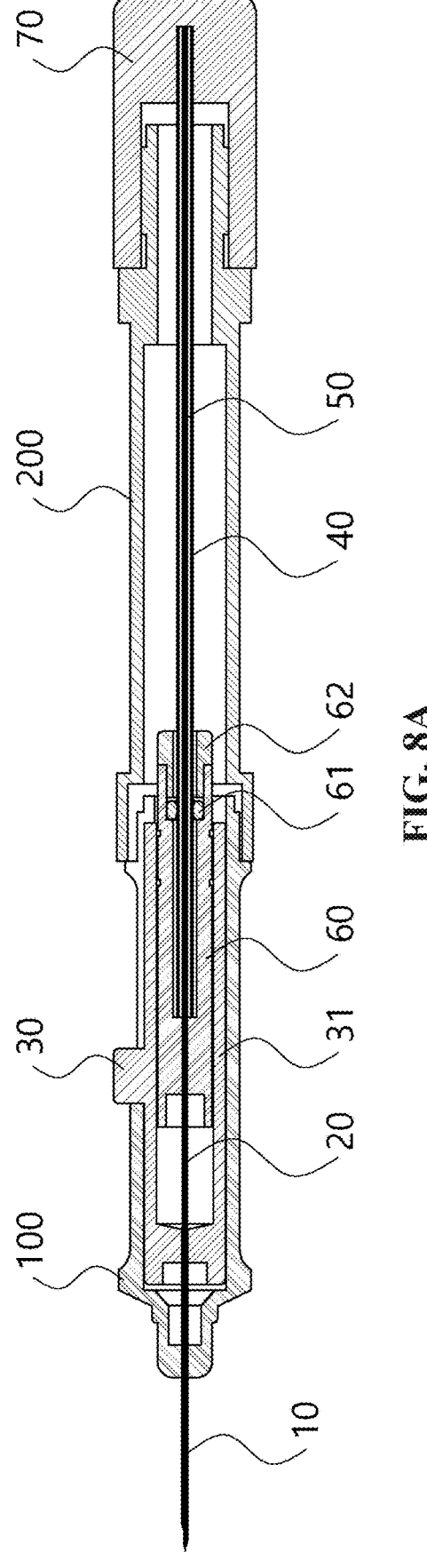
FIG. 8A is a view illustrating a state where a guide pin is advanced in the insertion device for a tube-type implant of FIG. 7A.
Figure 8B:
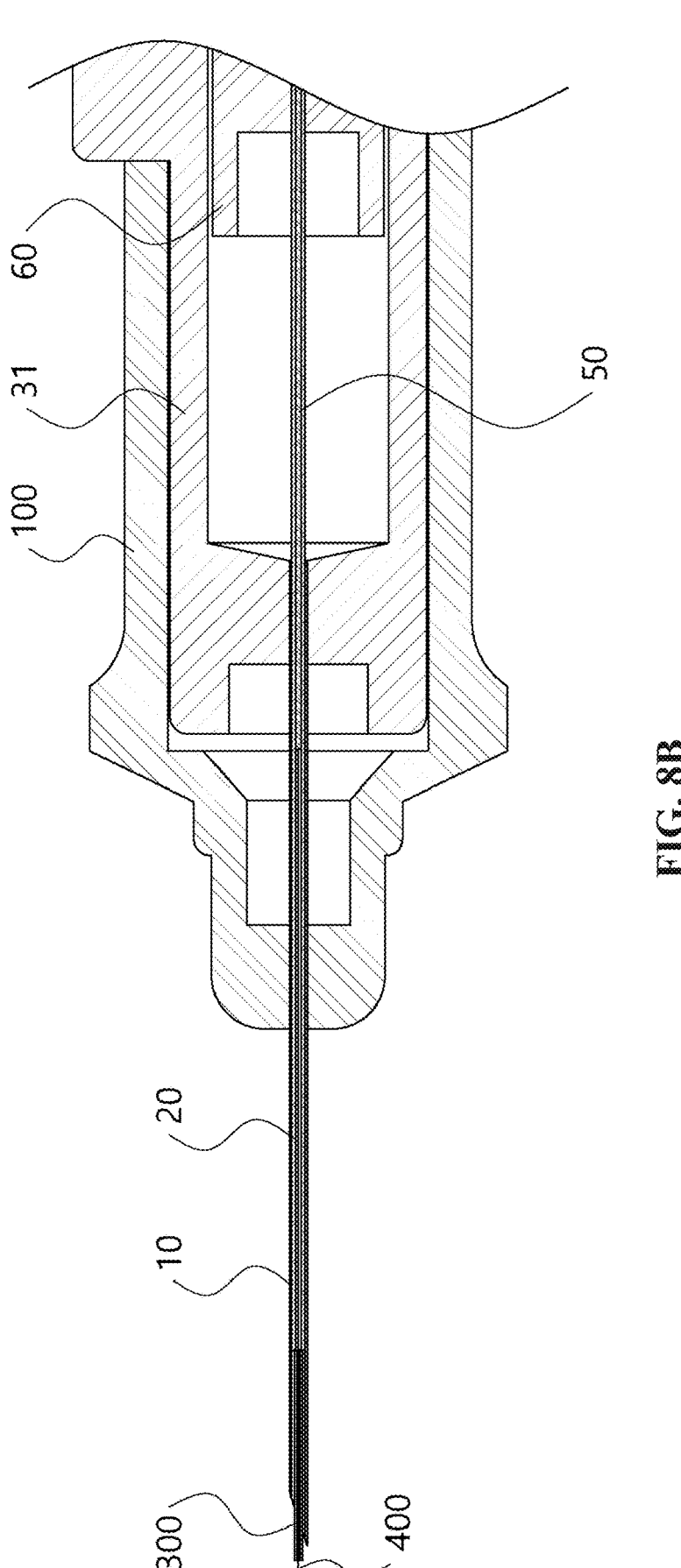
FIG. 8B is a partial cross-sectional view illustrating the insertion device for a tube-type implant of FIG. 8A.

After the implant 300 is placed in the insertion device, the guide pin 20 and the support rod 50 may be advanced by rotating the feed adjustment unit 70 to move the implant 300 forward. FIG. 8A is a view illustrating a state where a guide pin is advanced in the insertion device for a tube-type implant of FIG. 7A. FIG. 8B is a partial cross-sectional view illustrating the insertion device for a tube-type implant of FIG. 8A. As described with reference to FIGS. 4A to 4C, positions of the guide pin 20 and the support rod 50 may be adjusted by manipulating the feed adjustment unit 70 to use the implants 300 of various lengths and the ripcord 400. Also, after the needle 10 is inserted into an eyeball, the guide pin 20 and the support rod 50 may be advanced to the extent that the implant 300 is slightly exposed outside the needle 10 in order to check a position of the implant 300.

When the implant 300 is inserted at an insertion position in the eyeball, an operator may retract the needle 10 and the guide pin 20 by using the handle 30 so that only the implant 300 remains in the eyeball. In this case, a process of retracting the needle 10 and the guide pin 20 may include a step of retracting the needle 10 by partially retracting the handle 30 and a step of retracting the needle 10 and the guide pin 20 together by further retracting the handle 30.

Figure 9A:
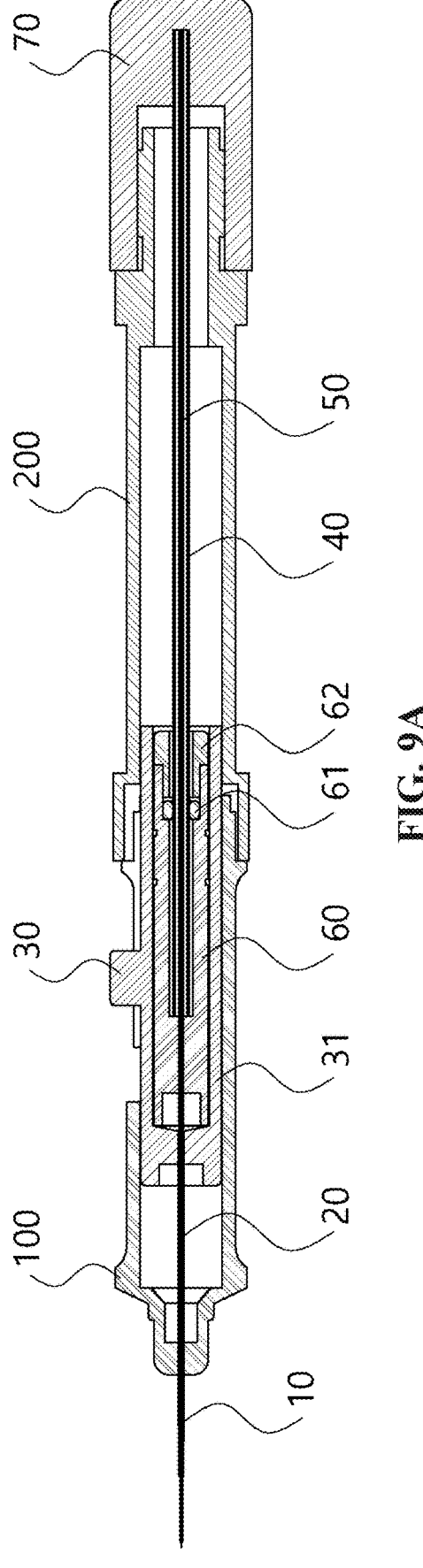
FIG. 9A is a view illustrating a state where a handle is partially retracted in the insertion device for a tube-type implant of FIG. 8A.
Figure 9B:
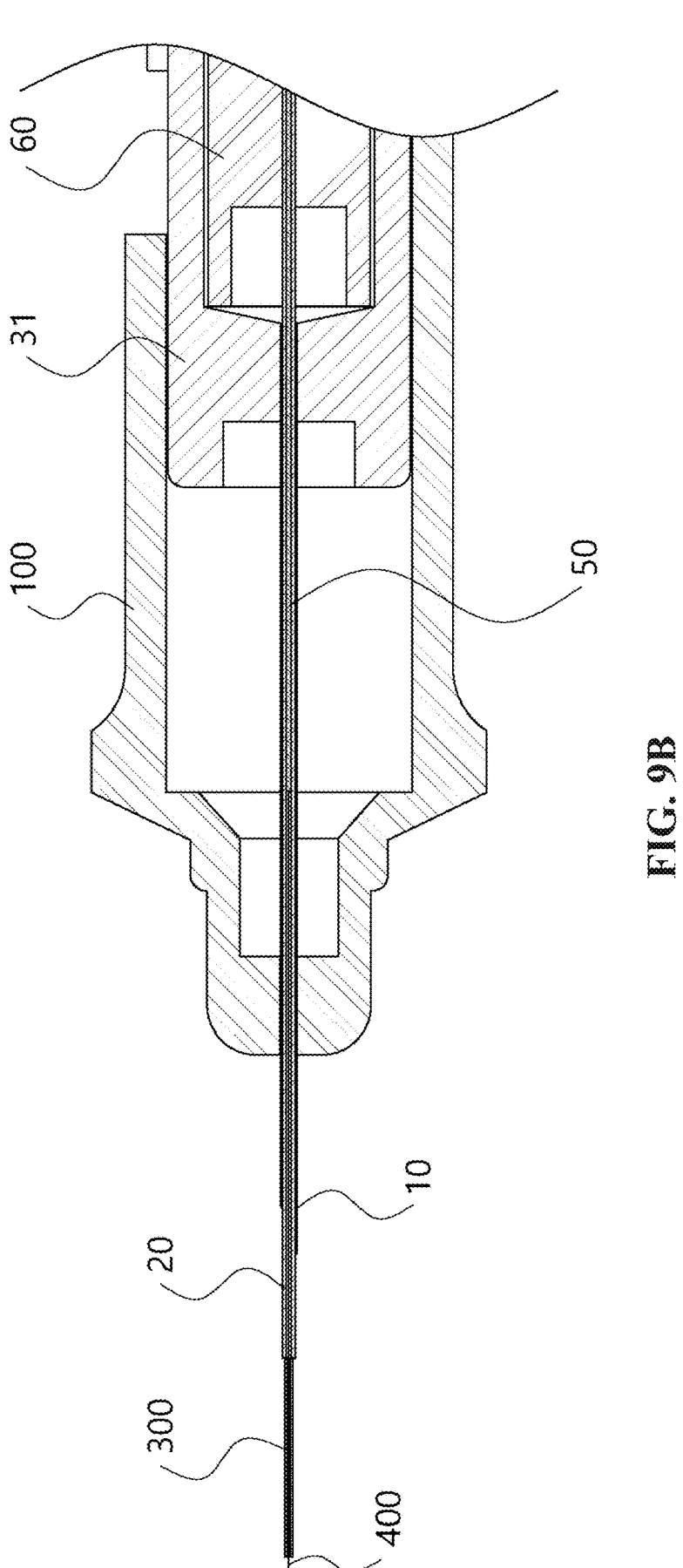
FIG. 9B is a partial cross-sectional view illustrating the insertion device for a tube-type implant of FIG. 9A.

FIG. 9A is a view illustrating a state where a handle is partially retracted in the insertion device for a tube-type implant of FIG. 8A. FIG. 9B is a partial cross-sectional view illustrating the insertion device for a tube-type implant of FIG. 9A.

Referring to FIGS. 9A and 9B, when the handle 30 is slid, the handle body 31 moves backward and the needle 10 connected to the handle body 31 is retracted. In this case, because the piston 60 is located behind the handle body 31 and the piston 60 is disposed to be at least partially inserted into the handle body 31, the handle 30 may be moved backward until an inner surface of the handle body 31 contacts the piston 60. In this state, when the operator applies more force to the handle 30, the handle body 31 and the piston 60 move backward together as shown in FIGS. 10A and 10B.

Figure 10A:
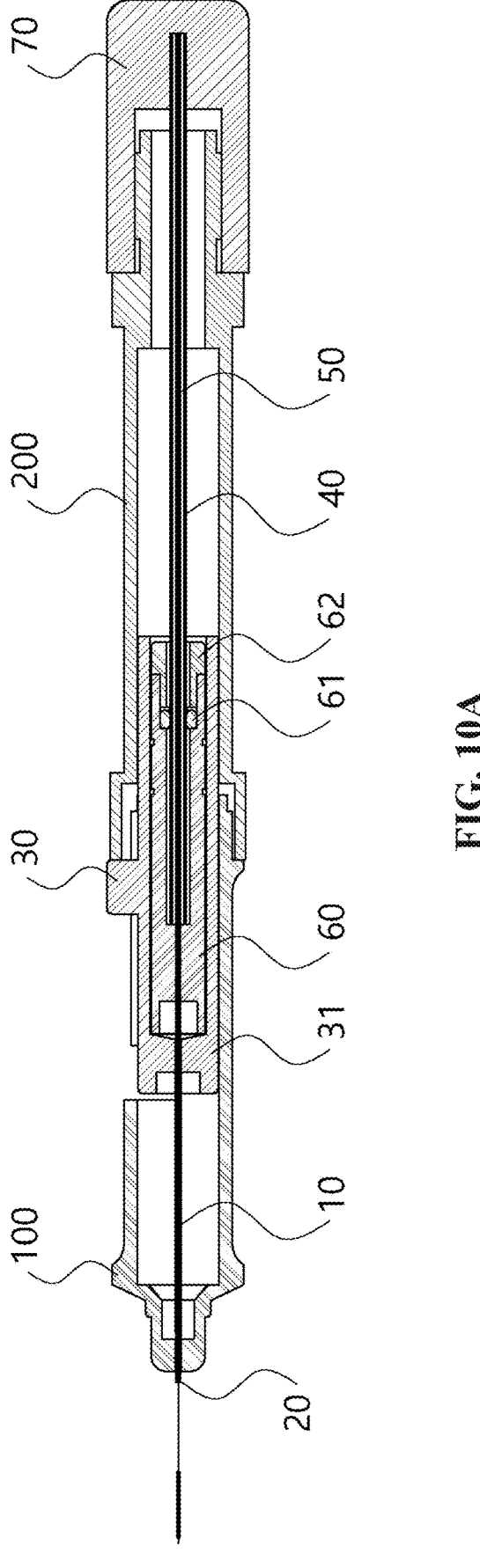
FIG. 10A is a view illustrating a state where a handle is further retracted in the insertion device for a tube-type implant of FIG. 9A.

FIG. 10A is a view illustrating a state where a handle is further retracted in the insertion device for a tube-type implant of FIG. 9A. FIG. 10B is a partial cross-sectional view illustrating the insertion device for a tube-type implant of FIG. 10A.

Figure 10B:
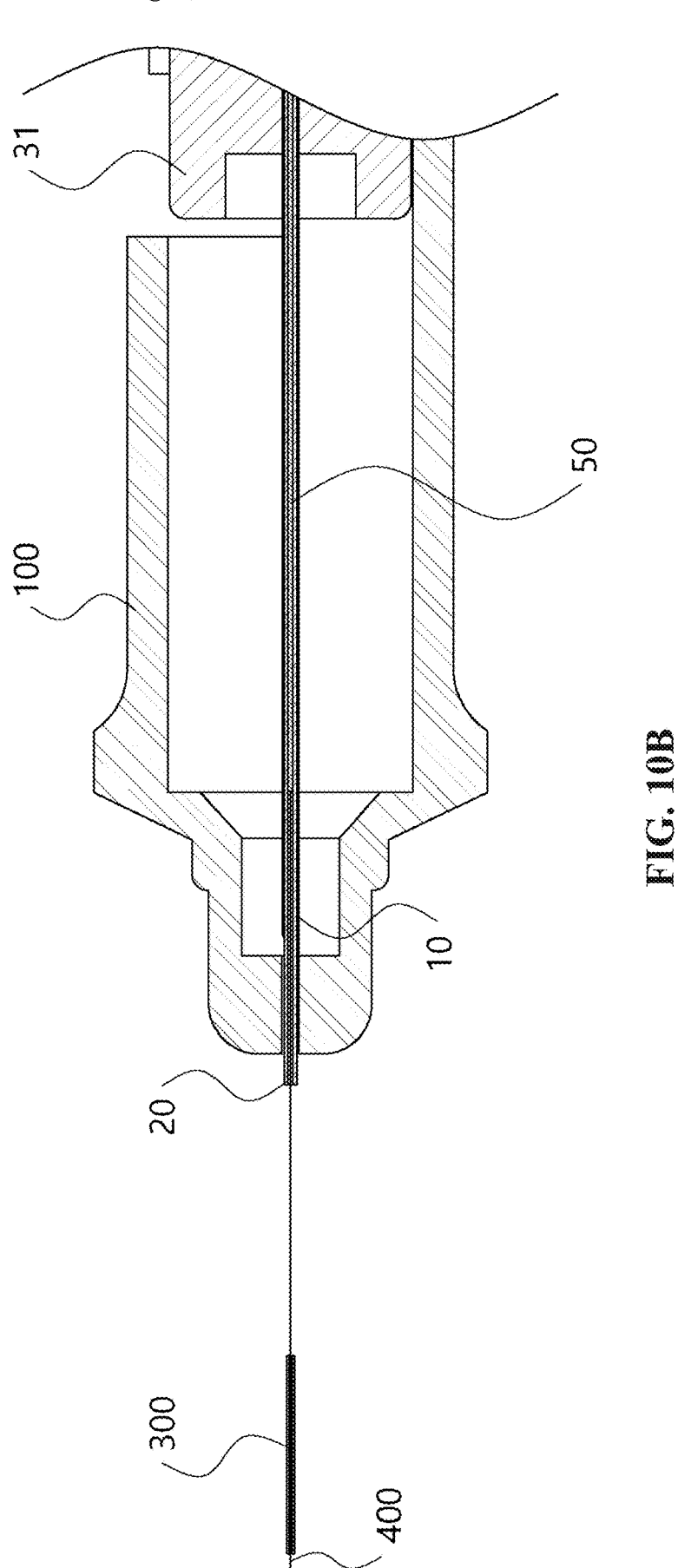
FIG. 10B is a partial cross-sectional view illustrating the insertion device for a tube-type implant of FIG. 10A.

Referring to FIGS. 10A and 10B, when the operator applies more force backward to the handle 30 in a state where an inner surface of the handle body 31 contacts the piston 60, the packing member 61 such as an O-ring disposed between the piston 60 and the pipe 40 slides and the piston 60 slides along an outer surface of the pipe 40. Accordingly, the handle body 31 and the piston 60 may move further backward at the same time as the operator applies force to the handle 30. Because the guide pin 20 is connected to the piston 60, the needle 10 is retracted by movement of the handle body 31 and at the same time, the guide pin 20 connected to the piston 60 is also retracted by the same distance.

As a result, all or most of the needle 10 and the guide pin 20 are accommodated inside the housing 100 and only the implant 300 remains outside the insertion device. In this case, the operator may place the implant 300 at a desired position in the eyeball by withdrawing the insertion device in a direction opposite to an insertion direction. The ripcord 400 inserted into the guide pin 20 of the insertion device is separated from the guide pin 20 while the operator withdraws the insertion device, and is located in the eyeball together with the implant 300.

Figure 11A:
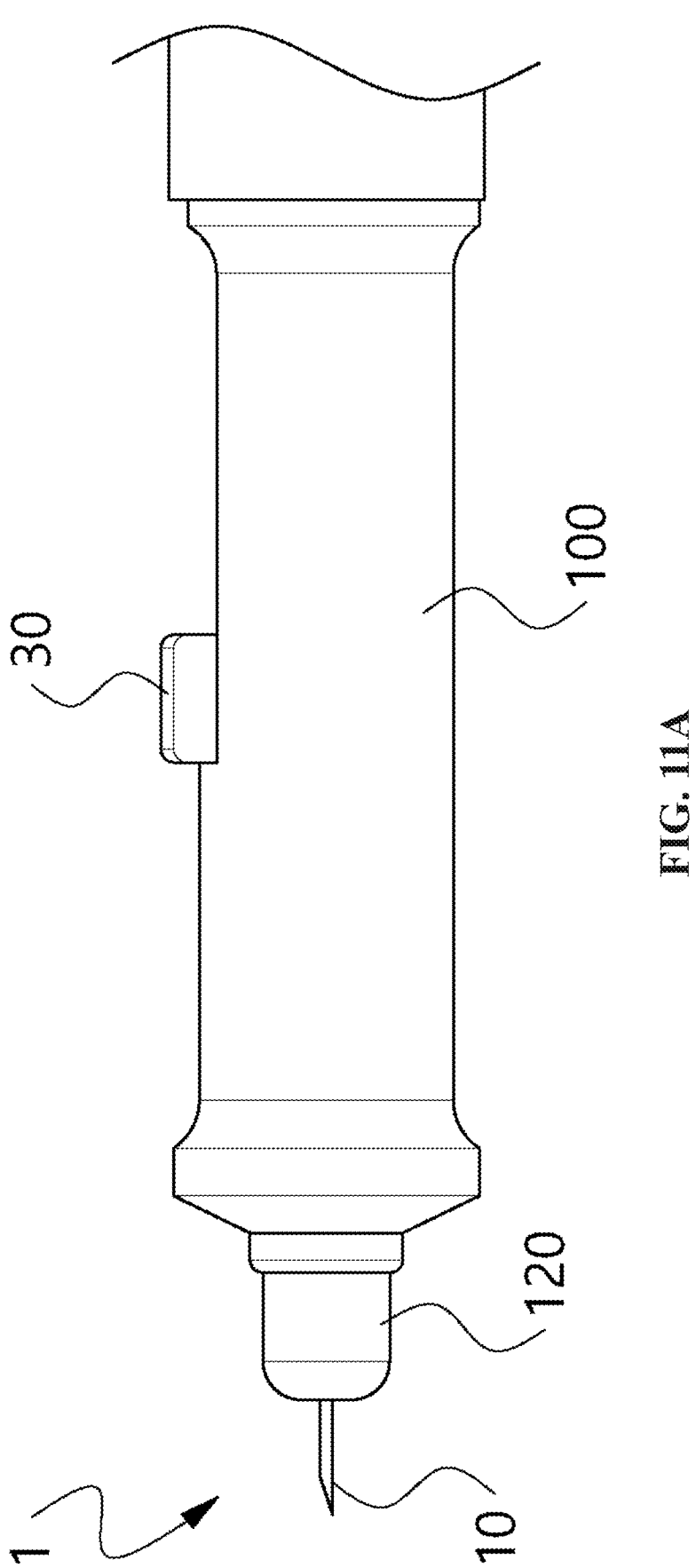
FIGS. 11A, 11B and 11C are views illustrating a stopper for preventing excessive insertion of a needle in an insertion device for a tube-type implant according to embodiments of the present disclosure.
Figure 11B:
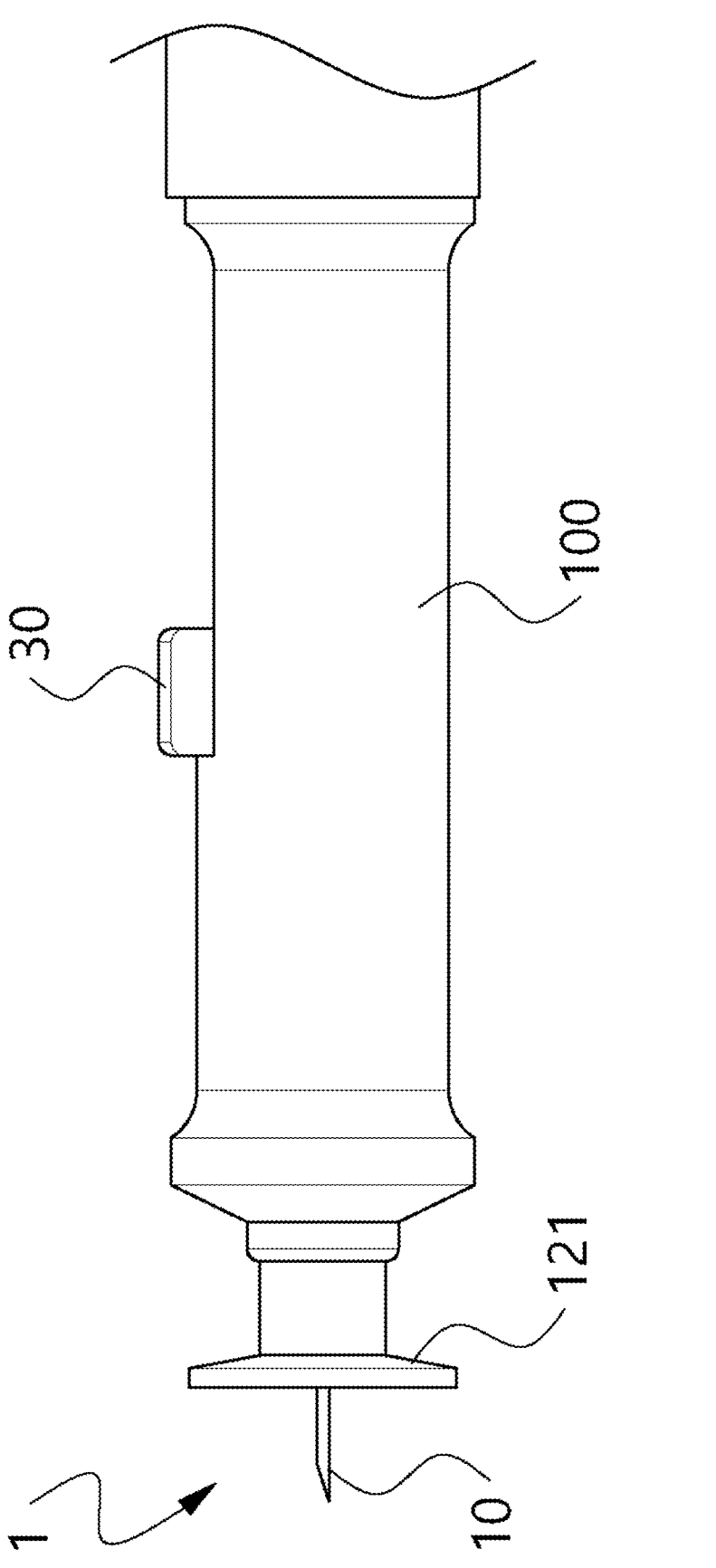
Figure 11C:
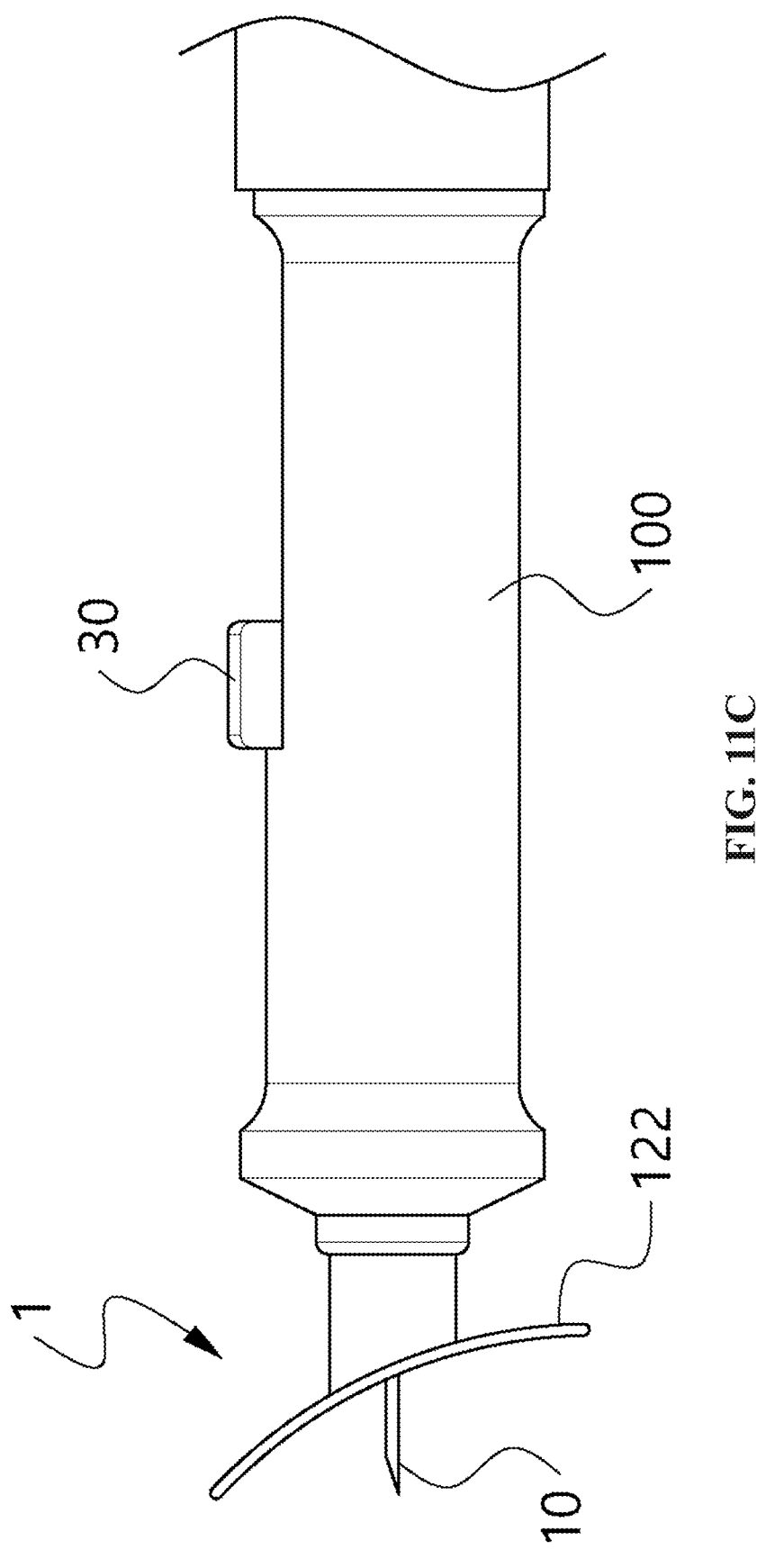

The insertion device for a tube-type implant according to embodiments may include a stopper for preventing a needle from being excessively inserted into an eyeball. FIGS. 11A to 11C are views illustrating a stopper for preventing excessive insertion of a needle in an insertion device for a tube-type implant according to embodiments of the present disclosure.

Referring to FIGS. 11A to 11C, the insertion device according to embodiments may include stoppers 120 to 122 each located at a front end of the housing 100 and having an increased diameter compared to the needle 10. In this case, the stoppers 120 to 122 are configured so that when an operator inserts an implant, the implant is caught on a sclera of an eyeball, and facilitate the operator's adjustment of an implant insertion position and prevent the needle 10 of the insertion device from being inserted too deeply into the eyeball to cause damage to the eyeball.

Referring to FIG. 11A, the stopper 120 may refer to an end of the housing 100 coupled to the needle 10. In this case, a diameter of the end of the housing 100 for functioning as the stopper 120 should be at least greater than a diameter of the needle 10, and a front end of the needle 10 should protrude by a certain length from the stopper 120 to enable the implant to be inserted.

Alternatively, referring to FIG. 11B, the stopper 121 may be a separate member coupled to or formed at an end of the housing 100 and having a larger diameter than the end of the housing 100 in order to be caught on the sclera. Furthermore, referring to FIG. 11C, the stopper 121 may have a curved shaper with a certain curvature corresponding to a curvature of a surface of the eyeball in order to prevent damage to the eyeball. However, shapes of the stoppers 120 to 122 shown in the drawings of the specification are only examples, and in embodiments, the stoppers may have any shape or structure that may contact the sclera so as to prevent the needle from being excessively inserted into the eyeball.

The above description of the present disclosure is provided for illustration, and it will be understood by one of ordinary skill in the art that various changes in form and details may be readily made therein without departing from essential features and the scope of the present disclosure. Accordingly, the above embodiments are examples only in all aspects and are not limited. For example, each component described as a single type may be executed in a distributed manner, and components described as a distributed type may be executed in a combined manner.

The scope of the present disclosure is indicated by the claims rather than by the detailed description of the present disclosure, and it should be understood that the claims and all modifications or modified forms drawn from the concept and scope of the claims and equivalents are included in the scope of the present disclosure.

INDUSTRIAL APPLICABILITY

Embodiments relate to an insertion device for a tube-type implant, and more particularly, relate to an insertion device that may easily insert an implant having a tube shape into an eyeball such as a tube for lowering intraocular pressure by draining aqueous humor in the eyeball and may minimize damage to the eyeball.

The invention claimed is:
1. An insertion device for a tube-type implant, comprising:

an implant having a tube shape for insertion into an eyeball, wherein the implant further comprises a ripcord inserted into the implant;

a needle having an inner space for accommodating the implant;

a handle connected to the needle for manipulation of a position of the needle; and a guide pin disposed to support the implant accommodated in the needle and having a hollow portion smaller than an outer diameter of the implant;

wherein the hollow portion of the guide pin is formed so that the ripcord is inserted into the hollow portion, and wherein the insertion device for a tube-type implant further comprises a support rod at least partially disposed in the guide pin to support the ripcord.

2. The insertion device for a tube-type implant according to claim 1, further comprising:

a handle body connecting the needle to the handle; and a housing in which the needle, the handle body, and the guide pin are accommodated, the housing comprising an opening extending in one direction, wherein the handle is exposed to outside through the opening of the housing and is configured to be slidable along the opening.

3. The insertion device for a tube-type implant according to claim 2, further comprising a feed adjustment unit coupled to one end of the housing and the guide pin to adjust a relative position of the guide pin with respect to the needle.

4. The insertion device for a tube-type implant according to claim 2, wherein the opening comprises a first portion extending in a first direction, and a second portion connected to the first portion from a second direction different from the first direction to limit movement of the handle along the first direction, wherein the handle body is disposed in the housing to be movable in the first direction and rotatable in the second direction.

5. The insertion device for a tube-type implant according to claim 2, further comprising a stopper formed at an end of the housing to limit movement of the housing into an eyeball.

6. The insertion device for a tube-type implant according to claim 5, wherein the stopper has a diameter greater than a diameter of the needle.

7. The insertion device for a tube-type implant according to claim 2, wherein the needle is coupled to the handle to selectively expose the implant to outside of the needle by sliding along an outer surface of the guide pin through manipulation of the handle.

8. The insertion device for a tube-type implant according to claim 7, further comprising a piston coupled to the guide pin and disposed in the housing to selectively contact the handle body through manipulation of the handle.

9. The insertion device for a tube-type implant according to claim 8, further comprising:

a pipe coupled to the housing and connected to the piston; and a packing member disposed between the piston and the pipe.

10. The insertion device for a tube-type implant according to claim 9, wherein the packing member is configured to allow relative movement of the piston with respect to the pipe through manipulation of the handle, in a state where the handle body is in contact with the piston.

11. The insertion device for a tube-type implant according to claim 1, further comprising one or more markers formed on a surface of the needle.

\* \* \* \* \*